US012299908B2

(12) United States Patent
Dacosta et al.

(10) Patent No.: US 12,299,908 B2
(45) Date of Patent: May 13, 2025

(54) MULTI-MODAL SYSTEM FOR VISUALIZATION AND ANALYSIS OF SURGICAL SPECIMENS

(71) Applicant: University Health Network, Toronto (CA)

(72) Inventors: Ralph S. Dacosta, Etobicoke (CA); Kathryn Ottolino-Perry, Toronto (CA); Christopher Gibson, Toronto (CA)

(73) Assignee: University Health Network, Toronto (CA)

( * ) Notice: Subject to any disclaimer, the term of this patent is extended or adjusted under 35 U.S.C. 154(b) by 397 days.

(21) Appl. No.: 17/423,597

(22) PCT Filed: Jan. 17, 2020

(86) PCT No.: PCT/IB2020/050381
§ 371 (c)(1),
(2) Date: Jul. 16, 2021

(87) PCT Pub. No.: WO2020/148722
PCT Pub. Date: Jul. 23, 2020

(65) Prior Publication Data
US 2022/0108461 A1   Apr. 7, 2022

Related U.S. Application Data

(60) Provisional application No. 62/793,715, filed on Jan. 17, 2019.

(51) Int. Cl.
*G06T 7/33* (2017.01)
*G01N 21/64* (2006.01)
(Continued)

(52) U.S. Cl.
CPC ........... *G06T 7/33* (2017.01); *G01N 21/6456* (2013.01); *G06T 7/38* (2017.01); *G16H 30/40* (2018.01);
(Continued)

(58) Field of Classification Search
CPC ... G06T 7/33; G06T 7/38; G06T 2207/10028; G06T 2207/10048; G06T 2207/10064;
(Continued)

(56) References Cited

U.S. PATENT DOCUMENTS 5,971,918 A    10/1999 Zanger
6,678,398 B2    1/2004 Wolters et al.
(Continued)

FOREIGN PATENT DOCUMENTS

CN    102027434    4/2011
CN    102099671    6/2011
(Continued)

OTHER PUBLICATIONS

First Examination Report dated Mar. 24, 2023 in related IN App No. 202117030691.
(Continued)

*Primary Examiner* — Dhaval V Patel
(74) *Attorney, Agent, or Firm* — Jones Robb, PLLC

(57) ABSTRACT

The present disclosure provides methods, systems, and devices for coregistering imaging data to form three-dimensional superimposed images of target such as a tumor or a surgical bed. A three-dimensional map can be generated by projecting infrared radiation at a target area, receiving reflected infrared radiation, and measuring depth of the target area. A three-dimensional white light image can be created from a captured two-dimensional white light image and the three-dimensional map. A three-dimensional fluorescence image can be created from a captured two-dimen-
(Continued)

sional fluorescence image and the three-dimensional map. The three-dimensional white light image and the three-dimensional fluorescence image can be aligned using one or more fiducial markers to form a three-dimensional superimposed image. The superimposed image can be used to excise cancerous tissues, for example, breast tumors. Images can be in the form of videos.

85 Claims, 25 Drawing Sheets

(51) Int. Cl.
    *G06T 7/38*     (2017.01)
    *G16H 30/40*     (2018.01)

(52) U.S. Cl.
    CPC .............. *G06T 2207/10028* (2013.01); *G06T 2207/10048* (2013.01); *G06T 2207/10064* (2013.01); *G06T 2207/10081* (2013.01); *G06T 2207/10088* (2013.01); *G06T 2207/10101* (2013.01); *G06T 2207/10136* (2013.01); *G06T 2207/30024* (2013.01); *G06T 2207/30096* (2013.01); *G06T 2207/30204* (2013.01)

(58) Field of Classification Search
CPC . G06T 2207/10081; G06T 2207/10088; G06T 2207/10101; G06T 2207/10136; G06T 2207/30024; G06T 2207/30096; G06T 2207/30204; G06T 17/20; G01N 21/6456; G16H 30/40; G01B 11/245; G01B 11/2513; G01S 17/46; G01S 17/894; G01S 17/86; G01S 17/89

See application file for complete search history.

(56) References Cited

U.S. PATENT DOCUMENTS

| | | | |
|---|---|---|---|
| 8,620,410 | B2 | 12/2013 | Frangioni |
| 9,326,666 | B2 | 5/2016 | Frangioni |
| 9,340,490 | B2 | 5/2016 | Okura et al. |
| 9,743,836 | B2 | 8/2017 | Tsubouchi et al. |
| 12,141,964 | B2 | 11/2024 | DaCosta et al. |
| 2005/0288594 | A1 | 12/2005 | Lewkowicz et al. |
| 2006/0249689 | A1 | 11/2006 | Eustergerling et al. |
| 2010/0145419 | A1 | 6/2010 | Fraval |
| 2010/0292580 | A1 | 11/2010 | Gilhuly et al. |
| 2011/0275900 | A1 | 11/2011 | Gilhuly et al. |
| 2012/0007950 | A1 | 1/2012 | Yang et al. |
| 2012/0016230 | A1* | 1/2012 | Kishima ................ A61B 1/045 600/425 |
| 2012/0051514 | A1* | 3/2012 | Sims .................... A61B 6/4417 378/63 |
| 2013/0215235 | A1 | 8/2013 | Russell |
| 2013/0338479 | A1 | 12/2013 | Pogue et al. |
| 2014/0218720 | A1 | 8/2014 | Kindem |
| 2014/0378843 | A1 | 12/2014 | Valdes et al. |
| 2015/0030542 | A1 | 1/2015 | Singhal |
| 2015/0038837 | A1 | 2/2015 | Inoue et al. |
| 2015/0150460 | A1 | 6/2015 | Krishnaswamy et al. |
| 2016/0206202 | A1 | 7/2016 | Frangioni |
| 2016/0278678 | A1 | 9/2016 | Valdes et al. |
| 2016/0377545 | A1 | 12/2016 | Wang |
| 2017/0059487 | A1 | 3/2017 | Wang |
| 2017/0085855 | A1 | 3/2017 | Roberts et al. |
| 2017/0235118 | A1 | 8/2017 | Kuster et al. |
| 2018/0114353 | A1* | 4/2018 | Champion ............ G06T 15/005 |
| 2018/0160047 | A1 | 6/2018 | Price et al. |
| 2018/0218508 | A1 | 8/2018 | Lee et al. |
| 2018/0242848 | A1 | 8/2018 | Dacosta et al. |
| 2018/0252909 | A1 | 9/2018 | Regensburger et al. |
| 2018/0276814 | A1 | 9/2018 | Frangioni |
| 2018/0279864 | A1 | 10/2018 | Frangioni |
| 2018/0325377 | A1 | 11/2018 | Dacosta et al. |
| 2019/0079011 | A1 | 3/2019 | Frangioni |
| 2019/0259162 | A1* | 8/2019 | Sartor ..................... G06T 7/521 |
| 2021/0051514 | A1 | 2/2021 | Li et al. |
| 2022/0092770 | A1 | 3/2022 | DaCosta et al. |
| 2023/0067762 | A1 | 3/2023 | Irrgang et al. |
| 2023/0280577 | A1 | 9/2023 | Valdes et al. |
| 2024/0197241 | A1 | 6/2024 | Barclay et al. |

FOREIGN PATENT DOCUMENTS

| | | |
|---|---|---|
| CN | 102314707 | 1/2012 |
| CN | 102370462 | 3/2012 |
| CN | 106803284 | 6/2017 |
| CN | 107093171 | 8/2017 |
| CN | 107851176 | 3/2018 |
| EP | 4322176 | 2/2024 |
| HK | 40108728 A | 11/2024 |
| JP | 2012023492 | 2/2012 |
| WO | 2004025556 | 3/2004 |
| WO | 2010080611 | 7/2010 |
| WO | 2013184830 | 12/2013 |
| WO | 2016063949 | 4/2016 |
| WO | 2017082242 | 5/2017 |
| WO | 2017096137 | 6/2017 |

OTHER PUBLICATIONS

Written Opinion dated Apr. 3, 2023 in related Application No. 11202107280U.
International Search Report and Written Opinion from International Application No. PCT/IB2020/050381, dated May 26, 2020.
International Search Report and Written Opinion from International Application No. PCT/IB2020/050380, dated May 14, 2020.
Office Action dated Jun. 29, 2022 in related CA application No. 2,955,976.
European Search Report dated Aug. 23, 2022 in related EP Application No. 20740945.9, 8 pages.
European Search Report dated Aug. 31, 2022 in related EP Application No. 20741439.2, 8 pages.
Office Action dated Dec. 6, 2022 in related CA Application No. 3,126,984.
Office Action dated Sep. 26, 2023 received in related JP Application No. 2021-541476.
Office Action dated Sep. 20, 2023 received in related CN Application No. 2020800219629.
European Search Report dated Feb. 15, 2024 received in related EP Application No. 23203744.0.
Office Action dated Mar. 4, 2024 received in related U.S. Appl. No. 17/423,449, 15 pp.
Office Action dated Mar. 26, 2024 received in related EP Application No. 20740945.9.
Examination Report dated Apr. 8, 2024 received in related SG Application No. 11202107280U.
Office Action dated Mar. 28, 2024 received in related CA Application No. 3,127,030.
Office Action dated Apr. 9, 2024 received in related JP Application No. 2021-541476.
Office Action dated Jun. 10, 2024 received in related Application No. MX/a/2021/008451.
Notice of Issuance dated Jun. 17, 2024 received in related CN Application No. 2020800219629.
Notice of Allowance dated Jul. 9, 2024 in related U.S. Appl. No. 17/423,449.
Corrected Notice of Allowability dated Aug. 21, 2024 received in related U.S. Appl. No. 17/423,449.
Examination Report dated Sep. 19, 2024 received in related AU Application No. 2020208842.
Office Action dated Oct. 18, 2024 received in related CA Application No. 3, 126,984.
Notice of Allowance dated Nov. 4, 2024 received in related Mexican Application No. MX/a/2021/008451.

(56) References Cited

OTHER PUBLICATIONS

Specification and Drawings for U.S. Appl. No. 18/943,247, filed Nov. 11, 2024.

* cited by examiner

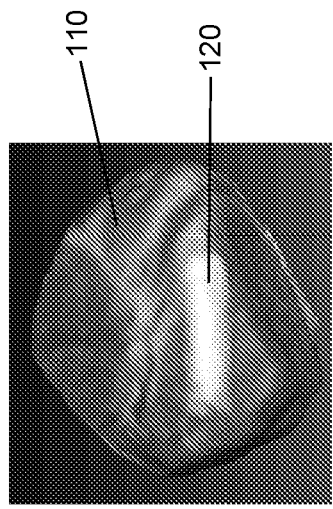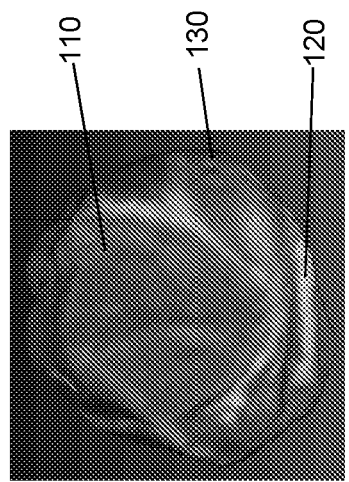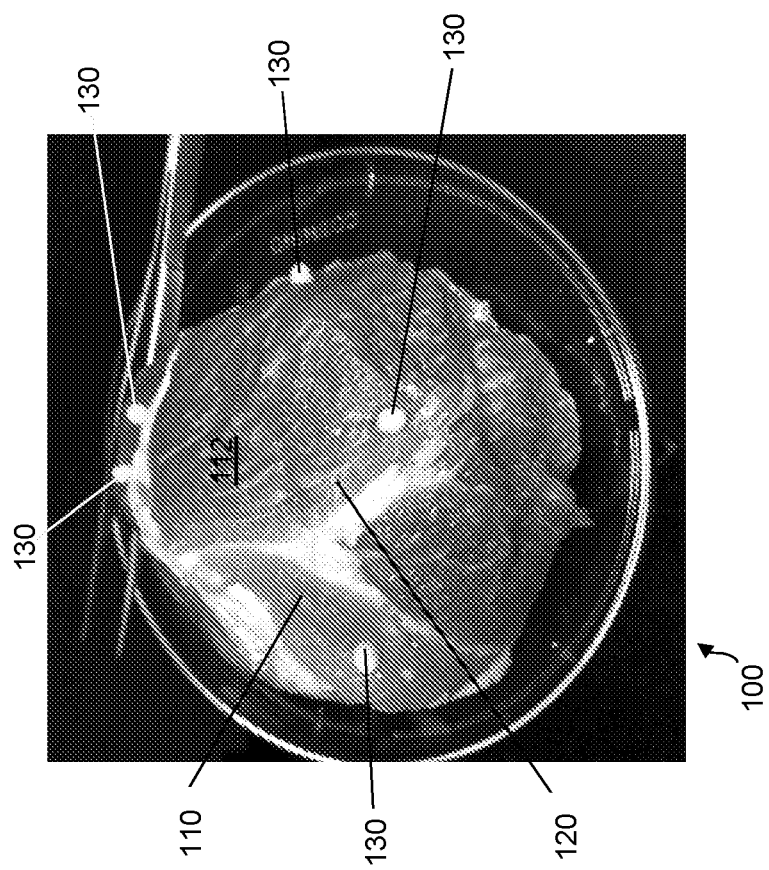

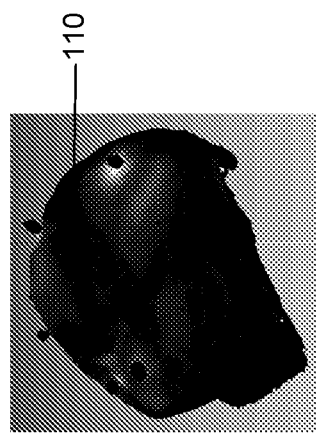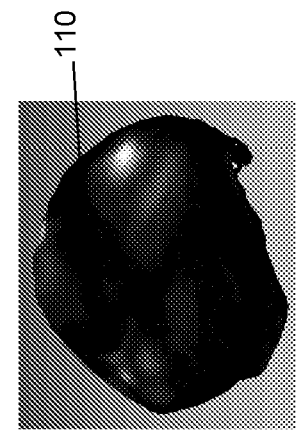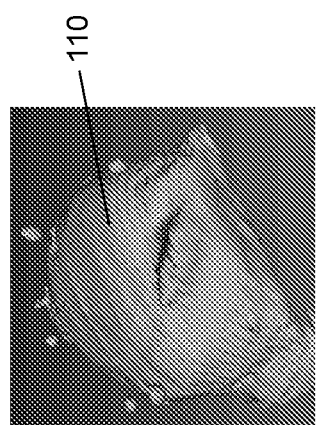
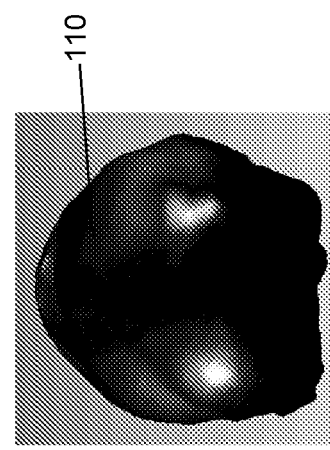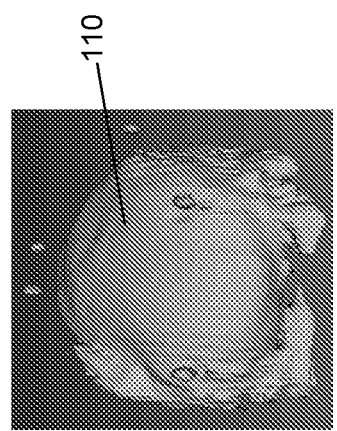
FIG. 13A  FIG. 13B  FIG. 13C
FIG. 14A  FIG. 14B  FIG. 14C

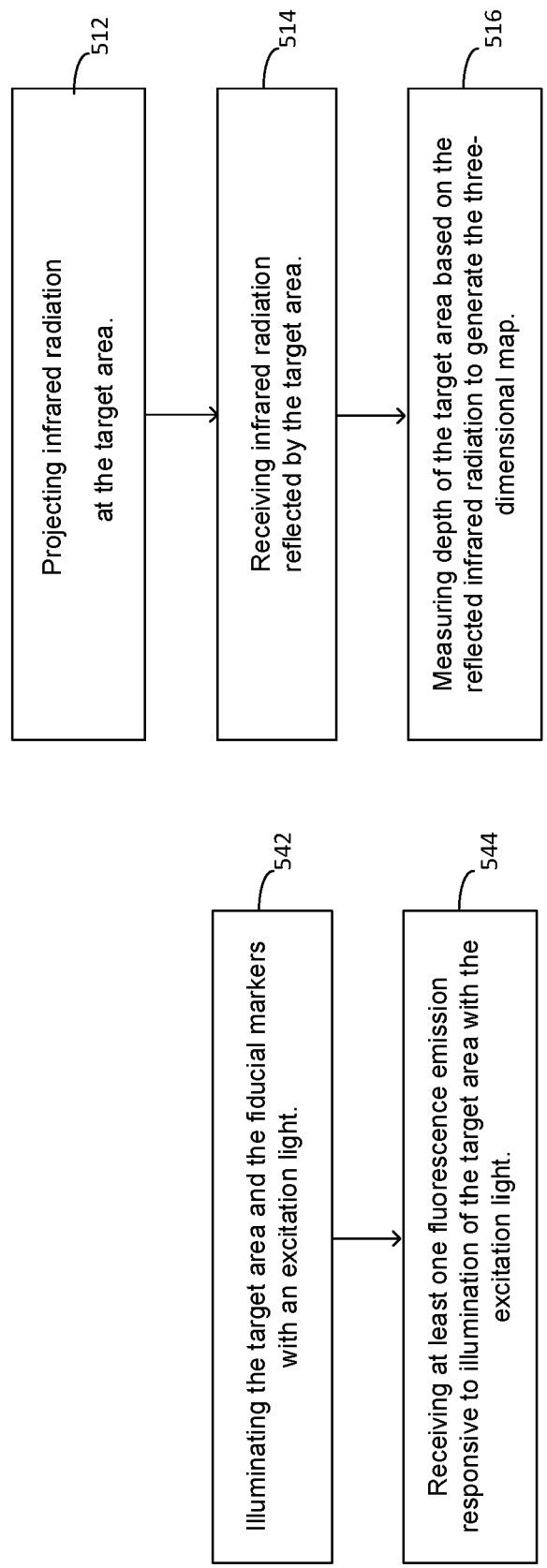

MULTI-MODAL SYSTEM FOR VISUALIZATION AND ANALYSIS OF SURGICAL SPECIMENS

CROSS REFERENCE TO RELATED APPLICATIONS

This patent application is a divisional application of U.S. patent application Ser. No. 17/423,449, filed Jul. 15, 2021, now U.S. Pat. No. 12,141,964 B2, which is a U.S. national stage application under 35 U.S.C. § 371(c) of International Application No. PCT/IB2020/050380, filed Jan. 17, 2020 which claims priority to U.S. Provisional Patent Application No. 62/793,715, filed Jan. 17, 2019, the entire content of each of which is incorporated herein by reference.

TECHNICAL FIELD

The present disclosure relates to systems for and methods of coregistering image data to create three-dimensional representations. The disclosure also relates to fluorescent imaging of lumpectomy tissues and other excised tissue specimens.

INTRODUCTION

Accurately identifying tumor margins on a lumpectomy or mastectomy surgical sample, as well as the corresponding surgical bed, remains a major problem in breast conservative surgery. Identifying the exact location of residual tumor tissues in the surgical bed when positive margins are found on the surgical sample also remains a challenge. Conventional approaches are suboptimal and are not performed in real time in the operating room. For example, conventionally, if a surgical sample has a positive margin, the surgeon removes the corresponding tumor in the surgical bed by shaving off substantially thick and laterally extensive layers of tissue in order to achieve negative margins. This imprecise procedure reduces the chances of preserving sufficient healthy breast tissue, making the conservation effort difficult. Similar issues exist for other cancers and procedures, for example, removal of melanoma. Characterization of tissue damage and pathologies, for example, wounds, as well as removal of tissues generally are in need of improved tools and techniques for greater precision and accuracy.

SUMMARY

The present disclosure can solve one or more of the above-mentioned problems and/or can demonstrate one or more of the above-mentioned desirable features. Other features and/or advantages are apparent from the description that follows.

In accordance with an aspect of the present disclosure, an imaging device is provided. The imaging device can comprise one or more of the following components and/or characteristics, for example, a chamber, an imaging system, and a data output system. A chamber can comprise a door comprising an interior door wall. The chamber can comprise a sidewall, a floor, and a ceiling. A sample platform can be configured to support a sample during imaging. An imaging system can be positioned within the chamber. The imaging system can comprise, for example, a fluorescence imaging subsystem, a visible light imaging subsystem, an infrared measuring subsystem, and at least one image sensor configured to detect radiation. A data output system can be configured to receive the detected radiation and to output data associated with the detected radiation. The imaging device can be configured to perform any suitable imaging protocol, for example, the imaging device can be configured to perform any method described herein, portion thereof, or modification thereof.

In accordance with an aspect of the present disclosure, a method of generating a three-dimensional image of a target using two-dimensional images obtained within an enclosed environment is provided. The method can comprise, for example, the following steps, while a target is positioned within the enclosed environment. A three-dimensional map of a target area associated with one or more fiducial markers can be generated. A two-dimensional white light image of the target area and the one or more fiducial markers can be captured. A two-dimensional fluorescence image of the target area and the one or more fiducial markers can be captured. The method can be performed in real time.

In accordance with an additional aspect of the present disclosure, an imaging device can comprise one or more of the following components. An excitation light source can be configured to emit a first radiation capable of exciting a fluorophore. A filter can be configured to prevent passage of reflected excitation light and permit passage of fluorescence emitted by the fluorophore. An imaging lens can be configured to focus radiation. A visible light source can be configured to emit a second radiation. An infrared light source can be configured to emit a third radiation. At least one image sensor can be configured to detect radiation. A processor can be configured to receive the detected radiation and to output data associated with the detected radiation. The imaging device can be configured to perform one or more of the methods, or portions thereof, described herein.

In accordance with an aspect of the present disclosure, a method of generating a three-dimensional image of a target using two-dimensional images is provided. The method can comprise, for example, the following. A three-dimensional map of a target area associated with one or more fiducial markers can be generated. A two-dimensional white light image of the target area and the one or more fiducial markers can be captured. The white light image can be substituted with a single wavelength or a combination of wavelengths constituting a subset of visible light wavelengths. A three-dimensional white light image can be created from the two-dimensional white light image and the three-dimensional map. A two-dimensional fluorescence image of the target area and the one or more fiducial markers can be captured. A three-dimensional fluorescence image can be created from the two-dimensional fluorescence image and the three-dimensional map. The three-dimensional white light image and the three-dimensional fluorescence image can be aligned using the one or more fiducial markers to form a three-dimensional superimposed image.

Additional objects and advantages of the present disclosure are set forth in part in the description which follows, and in part are apparent from the description, or can be learned by practice of the present disclosure. The objects and advantages of the present disclosure can be achieved by means of the elements and combinations particularly pointed out in the appended claims.

Both the foregoing general description and the following detailed description are exemplary and explanatory only and are not restrictive of the present disclosure, as claimed.

The accompanying drawings, which are incorporated in and constitute a part of this specification, illustrate several embodiments of the present disclosure and together with the description, serve to explain the principles of the present disclosure.

BRIEF DESCRIPTION OF DRAWINGS

FIG. 1 is a flow chart depicting a method of the present disclosure.

FIG. 2 is a flow chart depicting a method of the present disclosure.

DETAILED DESCRIPTION

Figure 4A:
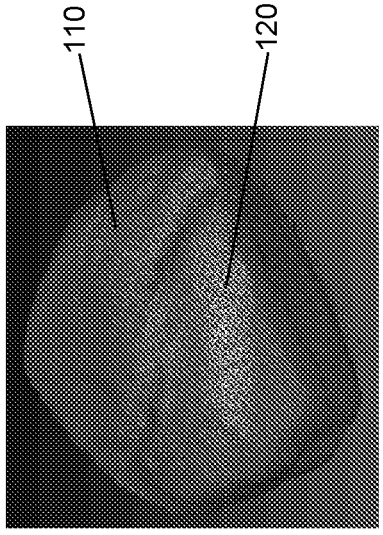
FIG. 4 is a flow chart depicting a method of the present disclosure.

The present disclosure enables the creation of three-dimensional images of an object that help a user better characterize and understand the object to achieve goals not previously possible or to more effectively achieve those goals than before. Image types that carry unique information can be combined in a manner that aids the user in visualizing a problem to more easily find a solution. Fluorescence images that carry information about the location of infected or cancerous tissue, when placed in the direct context of a white light image, can help a surgeon to more accurately remove affected tissue and minimize the need to operate again by showing the surgeon the information carried by the fluorescence in a more familiar context. Further, these images can be converted from a two-dimensional to a three-dimensional image for superimposition to guide the user in a model environment better approximating the actual object. Two-dimensional images can be converted to three-dimensional images by wrapping them around a three-dimensional map of the object. The three-dimensional map can take many forms, for example, a mesh, and can be generated using a variety of different techniques, for example, using infrared radiation and its interaction with the object. While the object can be a target area of a biological target, the object visualized is by no means limited to medical contexts. On the contrary, the methods, devices, systems, and programs of the present disclosure have applicability in a wide range of technological fields in which information provided by fluorescence is relevant, for example, in food safety, cosmetics, agriculture, horticulture, medicinal areas, veterinary fields, sanitization, security, border customs, quality control, and forensics. Images can include one or more of single images, a continuous set of images, a discontinuous set of images, a set of images from a common perspective (angle), a set of images from different perspectives (angles), a set of images using the same imaging technology, a set of images using different imaging technologies, a set of time lapsed images, and a video. A video can comprise one or more sets of images.

In accordance with the present disclosure, a method of generating a three-dimensional image of a target using two-dimensional images is provided. The method can comprise, for example, the following. A three-dimensional map of a target area associated with one or more fiducial markers can be generated. A two-dimensional white light image of the target area and the one or more fiducial markers can be captured. The white light image can be substituted with a single wavelength or a combination of wavelengths constituting a subset of visible light wavelengths. A three-dimensional white light image can be created from the two-dimensional white light image and the three-dimensional map. A two-dimensional fluorescence image of the target area and the one or more fiducial markers can be captured. A three-dimensional fluorescence image can be created from the two-dimensional fluorescence image and the three-dimensional map. The three-dimensional white light image and the three-dimensional fluorescence image can be aligned using the one or more fiducial markers to form a three-dimensional superimposed image. Examples of such steps designated as 110, 120, 130, 140, 150, and 160 are depicted in FIG. 1. The order of steps can be varied. Two-dimensional images can be superimposed and then collectively turned into a three-dimensional superimposed image using the three-dimensional map. The three-dimensional map can be in the form of a mesh.

The capturing of the two-dimensional fluorescence image of the target area and the one or more fiducial markers can be performed using any applicable technique. For example, the capturing can comprise illuminating the target area and the one or more fiducial markers with an excitation light and receiving at least one fluorescence emission responsive to illumination of the target area with the excitation light. Examples of such steps designated as 142 and 144 are depicted in FIG. 2. The excitation light can comprise one or more wavelengths. For example, the excitation light can be between about 400 nm and about 450 nm. A wavelength of about 405 nm is such an example. The capturing of the two-dimensional fluorescence image of the target area and the one or more fiducial markers can comprise capturing an emission of at least one fluorescent molecule. The at least one fluorescent molecule can comprise an endogenous molecule capable of fluorescing. The at least one fluorescent molecule can comprise an endogenous molecule capable of fluorescing induced by an exogenous molecule. Induction can be brought about, for example, by accumulation, or modification, or both of the endogenous molecule. The at least one fluorescent molecule can comprise an exogenous molecule capable of fluorescing, a molecule comprising an exogenously added moiety capable of fluorescing, or both. For example, the at least one fluorescent molecule can comprise aminolevulinic acid (ALA) induced porphyrin.

Figure 3A:
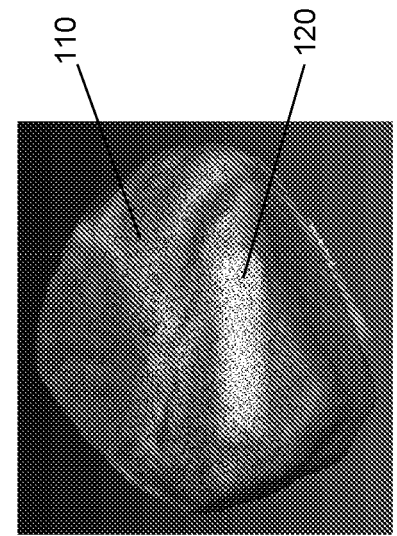
FIG. 3 is a flow chart depicting a method of the present disclosure.
Figure 3B:
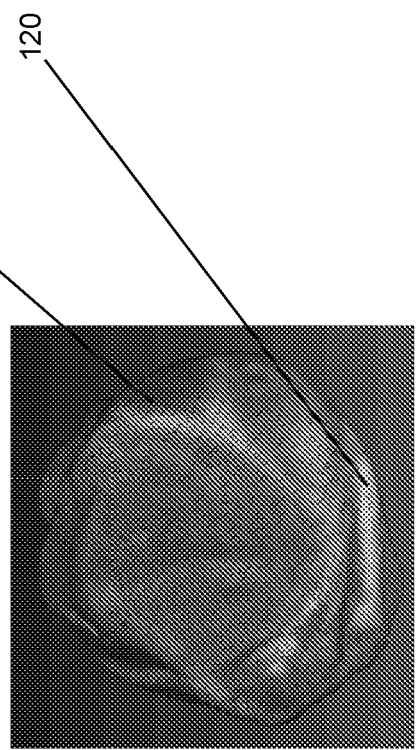

The three-dimensional map can be generated using any appropriate technique or combination of techniques. For example, the three-dimensional map can be generated using infrared light. The three-dimensional map can be generated using near infrared light. For example, generating the three-dimensional map can comprise projecting infrared radiation at the target area, receiving infrared radiation reflected by the target area, and measuring depth of the target area based on the reflected infrared radiation to generate the three-dimensional map. Examples of such steps designated as 112, 114, and 116 are depicted in FIG. 3. The infrared radiation can be projected as a beam split into a light pattern. The reflected infrared radiation can comprise a distortion of the light pattern, and the depth can be measured based on the distortion of the light pattern. The light pattern can be formed by a diffraction grating. The light pattern can comprise a plurality of dots of any size, shape, or intensity, or combination thereof. Alternative methods of measuring depth can be employed. For example, the depth can be measured by time-of-flight based on a phase shift between the projected and the reflected infrared radiation.

In accordance with the present disclosure, the following steps can be performed. One or more fiducial markers can be placed inside, along, and/or outside a perimeter of a target area on a surface of a biological target. A three-dimensional map of the target area can be generated by projecting infrared radiation at the target area, receiving infrared radiation reflected by the target area, and measuring depth of the target area based on the reflected infrared radiation to generate the three-dimensional map. A two-dimensional white light image of the target area and the one or more fiducial markers can be captured. The white light image can be substituted or generated with a single wavelength of light or a combination of wavelengths of light constituting a subset of visible light wavelengths. A three-dimensional white light image can be created from the two-dimensional white light image and the three-dimensional map. A two-dimensional fluorescence image of the target area and the one or more fiducial markers can be captured. The fluorescence two-dimensional image capturing can comprise exposing the target area and the one or more of fiducial markers to at least one wavelength capable of exciting at least one fluorescent molecule in the target area and receiving at least one fluorescence emission from the at least one fluorescent molecule in the target area through a filter. A three-dimensional fluorescence image can be created from the two-dimensional fluorescence image and the three-dimensional map. The three-dimensional white light image and the three-dimensional fluorescence image can be aligned using the one or more fiducial markers to form a three-dimensional superimposed image. The order of steps can be varied. Two-dimensional images can be superimposed and then collectively turned into a three-dimensional superimposed image using the three-dimensional map. The three-dimensional map can be in the form of a mesh.

The two-dimensional white light image, the two-dimensional fluorescence image, or any other image type described herein, can be captured using any suitable camera, imaging device, or image sensor. For example, the MolecuLight i:X imaging device available from MolecuLight Inc. of Toronto, Ontario, Canada, which includes a 5 megapixel camera, emits at 405 nm, and includes fluorescence emission filters of 500-545 nm and 600-665 nm respectively. An imaging device and associated methods described in U.S. Pat. No. 9,042,967, which is incorporated by reference in its entirety, can be used. Alternatively, one of the devices disclosed in U.S. Provisional Patent Application No. 62/625,967, filed Feb. 2, 2018 and entitled "Devices, Systems, and Methods for Tumor Visualization and Removal," U.S. Provisional Patent Application No. 62/625,983, filed Feb. 3, 2018 and entitled "Devices, Systems, and Methods for Tumor Visualization and Removal," and/or PCT/CA2019/000015, filed Feb. 1, 2019, entitled "Devices, Systems, and Methods for Tumor Visualization and Removal" and published as WO2019/148,268 on Aug. 8, 2019, the entire content of each of which is incorporated herein by reference, can be used to capture white-light images and/or fluorescence images.

A charged-coupled display (CCD), complementary metal-oxide-semiconductor (CMOS), N-type metal-oxide-semiconductor (NMOS), quantum Image Sensor (QIQ), or other image sensor, or combination thereof can be employed in capturing the two-dimensional white-light image, two-dimensional fluorescence image, or any other type of image described herein. The image can be captured using artificial and/or natural ambient light, one or more dedicated light sources, or a combination thereof. For example, the image can be captured using flash photography.

The source of white light can be full or partial spectrum visible light. For example, the white light spectrum can be from about 380 nm to about 740 nm, from about 400 nm to about 700 nm, from about 425 nm to about 690 nm, from about 450 nm to about 680 nm, or any intermediate range thereof. The source of white light can be produced directly or initially as white light, formed from sources of different wavelengths, a source of a defined wavelength or range of wavelengths shifted, for example, using quantum dots (QDots), to multiple wavelength or a wider spectrum of wavelengths, or any combination thereof. The white image can be substituted with or complemented by a different type of image, for example, a monochromatic color image, an infrared image, or an ultraviolet image, or any combination thereof.

Infrared radiation can be produced, projected, and received using any appropriate technique, device, or combination thereof. The infrared radiation can be projected as a beam split into a light pattern, the reflected infrared radiation can comprise a distortion of the light pattern, and the depth can be measured based on the distortion of the light pattern. Thus, the infrared radiation can comprise structured light. The light pattern can be formed by a diffraction grating and the light pattern can comprise a plurality of dots. The depth measurement can be determined using triangulation. The aforementioned infrared depth imaging can be used in the Microsoft Kinect I system (Microsoft Corporation, Redmond, Washington). Unstructured infrared radiation can be used additionally or in the alternative to structured infrared radiation. The depth can be additionally or alternatively measured by one or more time-of-flight (ToF) sensors, for example, based on a phase shift between the projected and reflected infrared radiation. This type of infrared depth imaging can be used in the Microsoft Kinect II system. Any suitable infrared camera, sensor, or imaging device, or combination thereof can be used.

The projected and/or reflected infrared radiation can be from about 700 nm to about 1.0 mm, from about 750 nm to about 1.0 µm, from about 1.0 µm to about 1.25 µm, from about 1.25 µm to about 1.5 µm, from about 1.5 µm to about 5.0 µm, from about 5.0 µm to about 15.0 µm, from about 15.0 µm to about 50 µm, from about 50 µm to about 150 µm, from about 150 µm to about 250 µm, from about 250 µm to about 500 µm, from about 500 µm to about 750 µm, or from about 750 µm to about 1.0 mm, or an intermediate range thereof, or a combination thereof. The infrared imaging can be performed in near infrared (for example, from about 0.75 µm to about 1.4 µm), short wavelength infrared (for example, from about 1.4 µm to about 3.0 µm), medium wavelength infrared (for example, from about 3.0 µm to about 8.0 µm), long wavelength infrared (for example, from about 8.0 µm to about 15 µm), far (very long wavelength) infrared (for example, from about 8.0 µm to about 1.0 mm), or any combination thereof.

The white light source, the fluorescence excitation light source, the infrared light source, or any other relevant light source for use in the present disclosure can be of any appropriate design or combination of designs. The light source can be coherent or incoherent, collimated or uncollimated, focused or unfocused, polarized or unpolarized, or any combination thereof. A light beam angle of less than about 1 degree, from about 1 degree to about 5 degrees, from about 5 degrees to about 15 degrees, from about 15 degrees to about 25 degrees, from about 25 degrees to about 35 degrees, from about 35 degrees to about 50 degrees, from about 50 degrees to about 75 degrees, from about 75 degrees to about 90 degrees, from about 90 degrees to about 120 degrees, from about 120 degrees to about 150 degrees, and from about 150 degrees to about 180 degrees can be used as the white light or other light source. One or more lasers and/or light emitting diodes (LED) can be used. A candescent, thermal, arc, incandescent, fluorescent, semiconductor-based, sodium vapor, or mercury vapor, or any combination or number thereof can be used as the light source. A single or multiple light source can be used. An array of light sources can be used.

The distance of the light source to the target to be imaged and/or measured can be, for example, from about 1.0 mm to about 10 m, from about 0.5 cm to about 5.0 m, from about 1.0 cm to about 2.5 m, from about 2.5 cm to about 1.0 m, from about 5.0 cm to about 0.5 m, from about 10.0 cm to about 0.25 m, or from about 25 cm to about 100 cm, or any intermediate distance thereof, or any combination thereof from the target area. Any number or type of light sources can be used. The light sources can be fixed or movable. The light sources can be integrated into the same device housing the camera, detector, or other imaging device, and/or can be external to such a device. The light source can be located internal or external to a target area or target volume. The one or more light sources can be articulated (for example, manually) to vary the illumination angle and spot size on the imaged surface, for example by using a built-in pivot, and can be powered, for example, through an electrical connection to a wall outlet and/or a separate portable rechargeable battery pack.

The fluorescence excitation wavelength can be matched to an emission wavelength of the one or more fluorophores targeted by the imaging. For example, the excitation wavelength can be from about 300 nm to about 325 nm, from about 325 nm to about 350 nm, from about 350 nm to about 375 nm, from about 375 nm to about 400 nm, from about 400 nm to about 425 nm, from about 425 nm to about 450 nm, from about 450 nm to about 475 nm, from about 475 nm to about 500 nm, from about 500 nm to about 525 nm, from about 525 nm to about 550 nm, from about 550 nm to about 575 nm, from about 575 nm to about 600 nm, from about 600 nm to about 625 nm, from about 625 nm to about 650 nm, from about 675 nm to about 700 nm, from about 750 nm to about 775 nm, from about 775 nm to about 800 nm, from about 800 nm to about 825 nm, from about 825 nm to about 850 nm, from about 850 nm to about 875 nm, from about 875 nm to about 900 nm, or from about 900 nm to about 1.0 mm, or any intermediate or overlapping range thereof, or any combination thereof.

The at least one fluorescence excitation wavelength can comprise a wavelength of, for example, 405 nm, with a spread of about 0.0 nm, from about 0.01 nm to about 0.05 nm, from about 0.5 nm to about 1.0 nm, from about 1.0 nm to about 2.5 nm, from about 2.5 nm to about 7.5 nm, from about 10 nm to about 25 nm, or from about 15 nm to about 30 nm, or an intermediate spread, or a combination thereof. The imaging device can use, for example, two violet/blue light (for example, 405 nm+/−10 nm emission, narrow emission spectrum) LED arrays (Opto Diode Corporation, Newbury Park, California), each situated on either side of the imaging detector assembly as the excitation or illumination light sources. These arrays have, for example, an output power of approximately 1 Watt each, emanating from a 2.5×2.5 $cm^2$ source, with a 70-degree illuminating beam angle. The LED arrays can be used to illuminate the tissue surface from a distance of about 10 cm, which means that the total optical power density on the skin surface can be about 0.08 $W/cm^2$.

The light signal produced by the light sources can be detected by the imaging device using one or more optical filters that reject the excitation light but allow selected wavelengths of emitted light from the tissue to be detected, thus forming an image on the display. Band-pass filters can be selected and aligned in front of a digital camera lens or other image detector or sensor to selectively detect specific optical signals from the target based on the wavelength of light desired. Spectral filtering of the detected optical signal (for example, absorption, fluorescence, and/or reflectance) can also employ a liquid crystal tunable filter (LCTF), or an acousto-optic tunable filter (AOTF) that can be a solid-state electronically tunable spectral band-pass filter. Spectral filtering can also involve the use of continuous variable filters, and/or manual band-pass optical filters. These devices can be placed in front of the imaging detector to produce multispectral, hyperspectral, and/or wavelength-selective imaging of a target area.

Optical or variably oriented polarization filters (for example, linear or circular combined with the use of optical wave plates) can be attached to the one or more light sources and/or the imaging device, sensor, or camera. These filters can permit imaging with polarized light illumination and non-polarized light detection or vice versa, or polarized light illumination and polarized light detection, with either white light reflectance and/or fluorescence imaging.

A PrimeSense camera (technology available from Apple Inc. of Cupertino, California), components thereof, or other sensors capable of three-dimensional imaging can be used in the techniques of the present disclosure. The PrimeSense camera includes a Carmine 1.08 sensor, a Carmine 1.09 (short range) sensor, and a Capri 1.25 (embedded) sensor. Depth acquisition can employ light coding technology. A scene can be scanned with near-infrared light. An infrared dot pattern can be emitted outward towards the target area. Light can be distorted when it contacts the target area and this distortion can be measured by the camera or other sensors, including, for example, a CMOS image sensor. An infrared camera sensor images the dot pattern on the target, simultaneously a white light RGB camera (adjacent to the infrared camera) captures a regular white light image of the target. The CMOS image sensor works with a visible video sensor to produce a depth map provided by PrimeSense System on a Chip (SoC)'s Carmine (PS1080) and Capri (PS1200) sensors that can be merged with a color image.

As an example, the PrimeSense device emits an (invisible to the naked eye) infrared dot pattern outward towards the target. An infrared camera sensor can image the dot pattern on the target, simultaneously a white light RGB camera (adjacent to the infrared camera) can capture a regular white light image of the target. The embedded software creates a "mesh" from the infrared dot pattern of the target topology. Then it wraps the white light image to that mesh topology using image (transforming function) morphing software code. The result is a white light image that can be transformed from two-dimensional to three-dimensional. The software used to run this process can be an open source software development kit (SDK) called OpenNI. Any appropriate software can be used. For example, OpenKinect or Microsoft Kinect Software Development Kit. A mesh or point cloud can also be created and manipulated using MeshLab.

In accordance with the present disclosure, a color image can alternatively or additionally be a fluorescence image. A registration process can be performed to align color image (RGB) and depth (D) information. The light coding infrared patterns can be deciphered in order to produce a VGA size depth image of the target area. The PrimeSense camera includes embedded software for image processing. Additional or alternative software can be employed. For example, open source SDK called OpenNI can be used. The embedded software creates a "mesh" from the infrared dot pattern of the target topology. Then it wraps the white light image to that mesh topology using image (transforming function) morphing software code. The result is a white light image that can be transformed from two-dimensional to three-dimensional. The PrimeSense camera can deliver visible video, depth, and audio information in a synchronized fashion via a USB 2.0 interface. An Xtion PRO LIVE camera (including an infrared dot projector, a RGB camera, and an infrared camera) available from ASUS Computer International (Fremont, California) can be used instead or in addition to a PrimeSense camera. A camera/sensor/projector system as described in U.S. Patent Application No. 2017/0054966, which incorporated by reference in its entirety, can be used. Time-of-flight infrared imaging can be used instead or in addition to structured light-based infrared imaging for depth measurement to obtain three-dimensional coordinate information of a target area.

Prior to imaging, fiduciary markers (for example, using an indelible fluorescent ink pen) can be placed on the surface of the skin, or other relevant surface, near the biological target edges or perimeter. For example, four spots, each of a different fluorescent ink color from separate indelible fluorescent ink pens, which can be provided as a kit to the clinical operator, can be placed near the target area margin or boundary on the normal skin surface. These colors can be imaged by the device using the excitation light and a multispectral band filter that matches the emission wavelength of the four ink spots. Image analysis can then be performed, by co-registering the fiduciary markers for inter-image alignment. This technique can facilitate longitudinal, time-sequence imaging of target areas, and the clinical operator can therefore image a target area over time without need for aligning the imaging device during every image acquisition.

To aid in intensity calibration of the fluorescence images, a disposable simple fluorescent standard "strip' can be placed into the field of view during target area imaging (for example, by using a mild adhesive that sticks the strip to the skin or other relevant surface temporarily). The strip can be impregnated with one or several different fluorescent dyes of varying concentrations which can produce predetermined and calibrated fluorescence intensities when illuminated by the excitation light source, which can have single (for example, 405 nm) or multiple fluorescence emission wavelengths or wavelength bands for image intensity calibration. The disposable strip can also have the four spots as described above (for example, each of different diameters or sizes and each of a different fluorescent ink color with a unique black dot placed next to it) from separate indelible fluorescent ink pens. With the strip placed near the target area margin or boundary on the normal skin surface, the device can be used to take white light and fluorescence images. The strip can offer a convenient way to take multiple images over time of a given target area and then align the images using image analysis. The fluorescent "intensity calibration" strip can also contain an added linear measuring apparatus, such as a ruler of fixed length to aid in spatial distance measurements of the target areas. Such a strip can be an example of a calibration target which can be used with the device to aid in calibration or measuring of image parameters (for example, target area size, fluorescence intensity, and the like). Other similar or functionally equivalent calibration targets can be used.

The one or more fiducial markers can comprise one or more fluorescent fiducial markers. For example, the one or more fluorescent fiducial markers can comprise fluorescein. The at least one fluorescent molecule can comprise an endogenous molecule capable of fluorescing, an exogenous molecule capable of fluorescing, or both. The at least one fluorescent molecule can comprise an endogenous molecule capable of fluorescing induced by an exogenous molecule. Induction can be brought about, for example, by accumulation, or modification, or both of the endogenous molecule. The at least one fluorescent molecule can comprise an exogenous molecule capable of fluorescing or a molecule comprising an exogenously added moiety capable of fluorescing. In an example, indocyanine green (ICG) can be excited at about 760 nm, at about 780 nm, or both. A filter comprising a notch from about 657 nm to about 825 nm can be used for 760 nm excitation. A filter comprising a notch from about 690 nm and about 840 nm can be used for 780 nm excitation.

The techniques described herein can detect a portion, a majority, or essentially all of tissue autofluorescence (AF). For example, using a multi-spectral band filter, tissue auto-fluorescence can be measured emanating from various tissue biomolecules, as well as blood-associated optical absorption, for example under 405 nm excitation: collagen (Types I, II, Ill, IV, V and others) which appear green, elastin which appears greenish-yellow-orange, reduced nicotinamide adenine dinucleotide (NADH), flavin adenine dinucleotide (FAD), which emit a blue-green autofluorescence signal, and bacteria/microorganisms, most of which can appear to have a broad (for example, green and red) autofluorescence emission. Image analysis can include calculating a ratio of red-to-green AF in the image. Intensity calculations can be obtained from regions of interest within the target area images. Pseudo-colored images can be mapped onto the white light images of the target area.

The at least one fluorescent molecule can comprise an induced endogenous fluorescent molecule, for example, aminolevulinic acid (ALA) induced porphyrins. ALA can be topically administered to the target area, and imaging can be performed 1-3 hours later for enhanced red fluorescence of target area bacteria. The pro-drug aminolevulinic acid (ALA) induces porphyrin formation in almost all living cells. Many bacteria species exposed to ALA are able to induce protoporphyrin IX (PpIX) fluorescence. The use of ultra-low dose ALA can induce PpIX formation in the bacteria and hence can increase the red fluorescence emission, which can enhance the red-to-green fluorescence contrast of the bacteria imaged with the device. ALA is non-fluorescent by itself, but PpIX is fluorescent at around 630 nm, 680 and 710 nm, with the 630 nm emission being the strongest. The imaging device can then be used to image the green and red fluorescence from the target area and the surrounding tissues.

A clinical operator can premix the ALA, which is usually provided commercially in lyophilized form with physiological saline or other type of commercially available cream/ ointment/hydrogel/dressing and the like, at a given dose and administer the agent topically by spraying it, pouring it, or carefully applying the agent to the target area prior to imaging. Approximately 10-30 minutes afterwards, although this time can vary, fluorescence imaging can be performed in a dimly lit or dark room. Bacteria under white light and perhaps poorly autofluorescent can appear as bright red fluorescent areas in and around the target area. The fluorescence images can be used to direct targeted swabbing, biopsy and/or fine needle aspirates of the target area for bacterial culturing based on the unique bacterial fluorescence signal. This procedure can be performed at different depths.

The techniques of the present disclosure can be used in conjunction with exogenous "pro-drug" agents, including, but not limited to, ALA, to increase the endogenous production of porphyrins in bacteria/microorganisms and thereby increase the intensities of unique 'porphyrin' fluorescence signals emanating from these bacteria to improve the detection sensitivity and specificity of the device. Thus, the techniques can be used to conveniently image photosensitizer-induced fluorescence (for example, PpIX) in bacteria or cancer cells for subsequent image-guided targeted swabbing/biopsy or treatment, for example using photodynamic therapy (PDT) or hyperbaric oxygen therapy (HOT). The techniques when used with for example consumable, commercially available fluorescence contrast agents have the ability to increase the signal-to-background for sensitive detection of bacteria, in and around target areas.

Suitable exogenous optical molecular targeting probes can be prepared using commercially available fluorescence labeling kits, such as the Alexa Fluor active esters and kits (for example, Zenon Antibody Labeling Kits and or EnzChek Protease Assay Kits, Invitrogen) for labeling proteins, monoclonal antibodies, nucleic acids and oligonucleotides (Invitrogen). For example, these fluorescent dye bioconjugates cover the following wavelength ranges: Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700 and Alexa Fluor 750 dyes, where the number stated refers to the excitation wavelength of the dye. These kits can offer well-differentiated fluorescence emission spectra, providing many options for multicolor fluorescence detection and fluorescence resonance energy transfer, based on the appropriate selection of fluorescence emission filters with the imaging device. The fluorescence dyes can offer high absorbance at wavelengths of maximal output of common excitation sources. They can be bright and unusually photostable to assist in achieving fluorescence of their bioconjugates. The dyes can offer good water solubility for ease of conjugation within the clinical exam room and resistance of the resulting conjugates to precipitation and aggregation. The fluorescence spectra of the dyes can be insensitive to pH over a broad range. In addition, other commercial or non-commercial fluorescent agents exist that can be appropriate for biological imaging and can be combined with the described device, including fluorescent blood pooling agents and various enzyme or protease activated probes from VisEn Medical (Boston, Mass., USA), for example.

These targeting fluorescent bioconjugates can be prepared using such labeling kits prior to the clinical exam of the target area using the imaging device in fluorescence mode. They can be stored in light-tight containers to avoid photobleaching. Such fluorescence bioconjugates can be prepared in solution at a known and appropriate concentration prior to fluorescence imaging of the target area using the device, and then administered/applied directly to the target area either topically (for example, via aerosol/spray), or given orally (for example, in a drink or lavage), or systemically (for example, via intravenous injection). Such dyes can target specific biological components depending on the targeting moiety, and can include, for example, one or more of bacteria, fungi, yeast, spores, virus, microbes, parasites, exudates, pH, blood vessels, reduced nicotinamide adenine dinucleotide (NADH), flavin adenine dinucleotide (FAD), microorganisms, specific types of connective tissues (for example, collagens, elastin), tissue components, vascular endothelial growth factor (VEGF), endothelial growth factor (EGF), epithelial growth factor, epithelial cell membrane antigen (ECMA), hypoxia inducible factor (HIF-1), carbonic anhydrase IX (CAIX), laminin, fibrin, fibronectin, fibroblast growth factor, transforming growth factors (TGF), fibroblast activation protein (FAP), enzymes (for example, caspases, matrix metalloproteinases (MMPs), and the like), tissue inhibitors of metalloproteinases (for example, TIMPs), nitric oxide synthase (NOS), inducible and endothelial NOS, lysosomes in cells, macrophages, neutrophils, lymphocytes, hepatocyte growth factor (HGF), anti-neuropeptides, neutral endopeptidase (NEP), granulocyte-macrophage colony stimulating factor (GM-CSF), neutrophil elastases, cathepsins, arginases, fibroblasts, endothelial cells, keratinocytes, keratinocyte growth factor (KGF), macrophage inflammatory protein-2 (MIP-2), macrophage inflammatory protein-2 (MIP-2), macrophage chemoattractant protein-1 (MCP-1), polymorphonuclear neutrophils (PMN) and macrophages, myofibroblasts, interleukin-1 (IL-1) and tumor necrosis factor (TNF), nitric oxide (NO) (Kit from Calbiochem, Model DAF-2 DA), c-myc, beta-catenin, and circulating endothelial progenitor cells (EPCs) from the bone marrow. Exogenous optical agents can include, for example, one or more of activated molecular beacons (for example, targeted), nanoparticles having fluorescent agents (for example, labeled on the surface and/or containing or carrying fluorescent agents), and scattering or absorbing nanoparticles (for example, gold, silver, and the like).

Commercially available organic fluorophores have properties that are dependent on hydrogen ion concentration, rendering them useful as probes for measuring pH, and they typically have pH sensitive UV/visible absorption properties. Commercially available pH sensitive fluorescent dyes employed in intracellular studies can provide a reduced fluorescent signal in acidic media or alternatively the pKa of the dye can be outside the intracellular pH window of between 5-8 pH units. However, other pH-sensitive fluorescent agents respond by increasing their fluorescence intensities. For example, Invitrogen Molecular Probes (Thermo Fisher Scientific) offers a variety of fluorescent pH indicators, their conjugates and other reagents for pH measurements in biological systems. Among these are several probes with unique optical response and specialized localization characteristics: for example, visible light-excitable SNARF pH indicators enable researchers to determine intracellular pH in the physiological range using dual-emission or dual-excitation ratiometric techniques, thus providing useful tools for confocal laser-scanning microscopy and flow cytometry. LysoSensor probes, as well as indicators based on the Oregon Green fluorophore, can be used to estimate the pH in a cell's acidic organelles. There are also fluorescent pH indicators coupled to dextrans that can be used. Following loading into cells, indicator dextrans can be well retained. Such fluorescent agents can be prepared in solution in advance at a known and appropriate concentration prior to fluorescence imaging of the target area using the device, and then administered/applied directly to the target area and surrounding normal tissues by one or more means, for example, topically (for example, via an aerosol and/or spray) orally, (for example, via a drink or lavage), or systemically (for example, via intravenous injection).

The biological target can comprise a tissue excised from a subject organism. For example, the tissue can comprise a precancerous or cancerous tissue. The cancerous tissue can comprise a tumor. For example, the tumor can be a breast tumor and the excised tissue can comprise a lumpectomy. The breast cancer can comprise any type or combination of types of breast cancer. For example, the breast cancer can be a luminal A breast cancer expressing cytokeratins 8 and 18 as well as high levels of estrogen receptor expression. The breast cancer can be a luminal B breast cancer. The breast cancer can be normal breast-like with respect to gene expression. The breast cancer can be HER2 amplified (amplification of the HER2 gene on chromosome 17q). The breast cancer type can be basal type that can be negative for certain receptors (estrogen, progesterone, and HER2) and have markers characteristic of basal/myoepithelial cells. A breast cancer can be characterized by one or more mutations in a BRCA1 gene, a BRCA2 gene, or both.

The cancerous tissue can be a pre-malignant growth, malignant growth, or tumor caused by abnormal and uncontrolled cell division that can be metastatic or non-metastatic. The tissue can be an excised tissue or tissue remaining in a tissue bed. The cancer can be, for example, breast cancer, prostate cancer, lung cancer, colon cancer, rectal cancer, urinary bladder cancer, non-Hodgkin lymphoma, melanoma, renal cancer, pancreatic cancer, cancer of the oral cavity, pharynx cancer, ovarian cancer, thyroid cancer, stomach cancer, brain cancer, multiple myeloma, esophageal cancer, liver cancer, cervical cancer, larynx cancer, cancer of the intrahepatic bile duct, acute myeloid leukemia, soft tissue cancer, small intestine cancer, testicular cancer, chronic lymphocytic leukemia, Hodgkin lymphoma, chronic myeloid cancer, acute lymphocytic cancer, cancer of the anus, anal canal, or anorectum, cancer of the vulva or cancer of the neck, gallbladder, or pleura, malignant mesothelioma, bone cancer, cancer of the joints, hypopharynx cancer, cancer of the eye, cancer of the nose, nasal cavity, neck, or middle ear, nasopharynx cancer, ureter cancer, peritoneum, omentum, or mesentery cancer, or gastrointestinal carcinoid tumor, or any combination thereof. The excised tissue can comprise a fluorescent molecule associated with a probe targeting a tumor receptor, an enzyme-activated fluorescent molecule, or a genetically modified oncolytic virus-induced fluorescence, or any combination thereof. For example, the tumor receptor can comprise HER2, a folate receptor, CXCR4, a hormone receptor, an EGFR, or a VEGF, or a combination thereof. Examples of hormone receptors include estrogen receptors and progesterone receptors. The enzyme can comprise, for example, a protease, a carbohydrase, a lipase, a transferase, an oxidoreductase, a matrix metalloprotease (MMP), a caspase, a cathepsin, a kallikrein, serine protease, isocitrate dehydrogenase, or an enzyme overexpressed by tumor cells, or a combination thereof.

The biological target can comprise a tissue excised from a surgical bed. The biological target can comprise the surgical bed from which a tissue has been excised. The excised tissue, the surgical bed, or both can comprise a precancerous tissue a cancerous tissue, or both. The cancerous tissue can be benign, malignant, or both. The tissue removed need not be cancerous and the techniques of the present disclosure can be used in other contexts, for example, plastic surgery, reconstructive surgery, organ transplant surgery, skin grafting, and cosmetic surgery.

The method can be performed any appropriate number of times. For example, the method can be performed at least twice, in either order, the two performances comprising a first performance and a second performance. The first performance can be performed on the biological target. For example, the biological target being a first biological target comprising an excised tissue. The second performance can be performed outside of the enclosed environment on a second biological target comprising a surgical bed from which the tissue is excised. The three-dimensional superimposed image of the first performance can be a first three-dimensional superimposed image and the three-dimensional superimposed image of the second performance can be a second three-dimensional superimposed image. The method can further comprise comparing the first and second three-dimensional superimposed images to determine a fluorescent continuity between the excised tissue and the surgical bed based on an orientation of the excised tissue relative to the surgical bed. The fluorescent continuity can comprise, for example, one or more of a bacterially infected tissue, a virally infected tissue, a burn, a cancerous tissue, a connective tissue, a muscle tissue, a blood vesicle, and a skin feature. The fluorescent continuity can correspond to a compromised tissue and the method can further comprise excising at least a portion of the compromised tissue from the surgical bed.

Figure 4B:
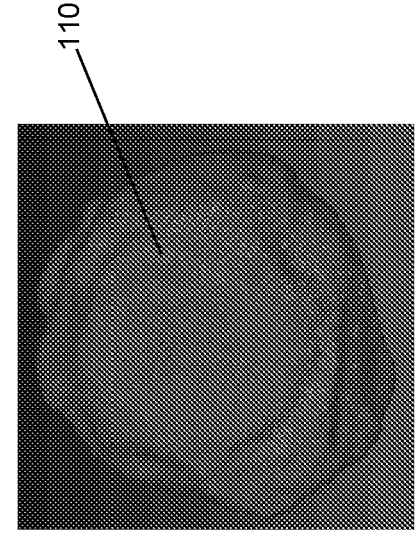

The method can comprise, for example, capturing a companion three-dimensional image of the target area and the one or more fiducial markers using an imaging technique comprising, for example, one or more of computerized tomography (CT), magnetic resonance imaging (MRI), photoacoustic imaging, ultrasound, and optical coherence tomography. The three-dimensional superimposed image can be superimposed with the companion three-dimensional image to form a second three-dimensional superimposed image. Examples of such steps designated as 170 and 180 are depicted in FIG. 4. The capturing of the companion three-dimensional image can comprise a single set or two or more sets of fiducial markers, for example, first and second sets of fiducial markers. Any suitable number or type of fiducial marker can be employed. Any suitable number of sets of fiducial markers can be employed. The number of fiducial markers employed can comprise, for example, 1, 2, 3, 4, 5, 6, 7, 8, 9, 10, 12, 15, 20, or 25, or more fiducial markers. The number of sets of fiducial makers employed can be 1, 2, 3, 4, or 5, or more sets. Sets can vary with respect to one or more of placement, size, fluorescence spectrum, fluorescence intensity, and imagining technology specificity of the fiducial markers. Different types of fiducial markers can be colocalized. The companion three-dimensional image can be captured using computerized tomography, and the one or more fiducial markers can comprise at least one fluorescent molecule and at least one CT contrast agent. The companion three-dimensional image can be captured using photoacoustic imaging, the target area can comprise a breast tumor, and the at least one fluorescent molecule can comprise an anti-HER2 dual fluorescence-photoacoustic probe.

The disclosure enables digital integration of pathology data, for example, from histology samples such as those employing a hematoxylin and eosin stain in a three-dimensional data cube of multiple imaging modalities. The data cube permits spatially-localized digital archiving and documenting of location-specific histopathology or other data from the tissue surface of either an ex vivo surgical sample or the surgical bed of a given patient over time. The sites of biopsies can be chronologically catalogued in digital format with corresponding pathology results or other relevant information such as suture site, anastomosis site, implant site, and the like. The cataloging allows a clinical team to tract where tissues have been sampled, the pathology at those sites, and these can be compared before and after a treatment. If tissue deformation occurs in an ex vivo surgical sample, image deformation correction models can be applied to account for the deformation and align with the topographical surface of the surgical bed.

The present disclosure provides a method of spatiotemporally co-registering multimodal imaging two-dimensional and three-dimensional data sets of biological tissues. Further provided are fluorescence and photoacoustic imaging techniques that work in concert with exogenously applied tumor contrast agents to increase the accuracy of detection of tumor cells at surgical margins. The present disclosure provides a clinically useful approach for hybridized surface and volumetric imaging technologies to improve surgical planning, intraoperative guidance, and margin assessment. Otherwise subclinical tumor margins can be identified. Cancer diagnosis can be improved by combining optical imaging data sets (for example, from one or more of photoacoustics, fluorescence, optical coherence tomography (OCT), and Raman imaging) including with traditional MRI, CT, PET, and/or US scans for tumor diagnosis and response assessment. The disclosed methods, devices, and system also allow for endoscopic imaging and general research.

In accordance with the present disclosure, an imaging device is provided. The imaging device can comprise one or more of the following components. An excitation light source can be configured to emit a first radiation capable of exciting a fluorophore. A filter can be configured to prevent passage of reflected excitation light and permit passage of fluorescence emitted by the fluorophore. An imaging lens can be configured to focus radiation. A visible light source can be configured to emit a second radiation. An infrared light source can be configured to emit a third radiation. At least one image sensor can be configured to detect radiation. A processor can be configured to receive the detected radiation and to output data associated with the detected radiation. The imaging device can be configured to perform one or more of the methods, or portions thereof, described herein.

The imaging device can be configured to visualize any appropriate target area of a biological target, other kind of target, or a combination thereof. The imaging device can be configured to visualize, for example, one or more of a precancerous cell, a cancerous cell, and a satellite lesion in a surgical margin. The excitation light source can be further configured to excite autofluorescence emissions of tissue cells and fluorescence emissions of induced porphyrins in tissue cells of the surgical margin. The filter can be further configured to prevent passage of reflected excitation light and permit passage of emissions having a wavelength corresponding to the autofluorescence emissions of the tissue cells and the fluorescence emissions of the induced porphyrins in the tissue cells. The image sensor can be further configured to detect the filtered autofluorescence emissions of the tissue cells and the fluorescence emissions of the induced porphyrins in the tissue cells of the surgical margin. The processor can be further configured to receive the detected emissions and to output data regarding the detected filtered autofluorescence emissions of the tissue cells and the fluorescence emissions of the induced porphyrins in the tissue cells of the surgical margin.

The detected radiation can comprise one or more of fluorescence, reflected visible light, and reflected infrared light. The detected radiation can comprise fluorescence, reflected visible light, and reflected infrared light. The first radiation can comprise fluorescence. The second radiation can comprise, for example, white light. The second radiation can comprise monochromatic visible light. The third radiation can comprise infrared radiation, for example, near infrared radiation. The at least one image sensor can be configured to detect radiation comprising one or more of fluorescence, reflected visible light, and reflected infrared light. The at least one sensor can comprise any number and/or type of sensor, for example, at least two sensors. The at least two sensors can comprise a first sensor configured to detect fluorescence and a second detector configured to detect reflected visible light. The at least one sensor can comprise at least three sensors comprising a first sensor configured to detect fluorescence, a second detector configured to detect the reflected visible light, and a third sensor configured to detect reflected infrared light.

The imaging device can further comprise a common radiation source configured to operate with one or more of the light sources. The one or more light sources can comprise a converter to convert source radiation emitted from the common radiation source to the first radiation, the second radiation, or the third radiation, or a combination thereof. The converter can comprise, for example, a filter, a lens, a prism, a diffractor, or a quantum dot, or a combination thereof. The excitation light source can comprise a first converter, the visible light source can comprise a second converter, and the infrared light source can comprise a third converter.

The imaging device can further comprise a display unit. Any display unit can be used, for example, a liquid crystal display (LCD), a light emitting display (LED), an organic light emitting display (OLED), plasma, or cathode ray, or any combination thereof. The display unit can be configured to display the data output by the processor. For example, the data can comprise a three-dimensional image. The display unit can comprise a touchscreen and/or any other type of graphic user interface. A display unit can alternatively or additionally be located in a device other than the imaging device.

The imaging device can be configured to visualize a target area of a biological target. The processor can be configured to generate a three-dimensional map of the target area. The three-dimensional map can be generated from infrared light reflected from the target area. The processor can be configured to capture a two-dimensional visible light image of the target area based on the detected radiation. The processor can be configured to create a three-dimensional visible light image of the target area based on the three-dimensional map and the two-dimensional visible light image. The processor can be configured to capture a two-dimensional fluorescence image of the target area based on the detected radiation. The processor can be configured to create a three-dimensional fluorescence image of the target area based on the three-dimensional map and the two-dimensional fluorescence image. The processor can be configured to align a three-dimensional visible light image of the target area with a three-dimensional fluorescence image of the target area to form a three-dimensional superimposed image of the target area. The alignment can be performed based on co-registration of one or more fiducial markers associated with the target area.

In accordance with the present disclosure, a method of generating a three-dimensional image of a target using two-dimensional images obtained within an enclosed environment is provided. The method can comprise, for example, the following steps, while a target can be positioned within the enclosed environment. A three-dimensional map of a target area associated with one or more fiducial markers can be generated. A two-dimensional white light image of the target area and the one or more fiducial markers can be captured. A two-dimensional fluorescence image of the target area and the one or more fiducial markers can be captured. The method can be performed in real time.

The capturing of the two-dimensional fluorescence image of the target area and the one or more fiducial markers can comprise, for example, the following steps. The target area and the one or more fiducial markers can be illuminated with an excitation light. At least one fluorescence emission responsive to illumination of the target area with the excitation light can be received. The excitation light can be, for example, between about 400 nm and about 450 nm, such as a wavelength of about 405 nm. The capturing of the two-dimensional fluorescence image of the target area and the one or more fiducial markers can comprise capturing an emission of at least one fluorescent molecule. The at least one fluorescent molecule can comprise an endogenous molecule capable of fluorescing. The at least one fluorescent molecule can comprise an exogenous molecule capable of fluorescing or a molecule comprising an exogenously added moiety capable of fluorescing. The at least one fluorescent molecule can comprise aminolevulinic acid (ALA) induced porphyrins.

The three-dimensional map can be generated using infrared light, for example, near infrared light. The three-dimensional map can be generated, for example, by the following steps. Infrared radiation can be projected at the target area. Infrared radiation reflected by the target area can be received. The depth (topography) of the target area can be measured based on the reflected infrared radiation to generate the three-dimensional map. The infrared radiation can be projected as a beam split into a light pattern. The reflected infrared radiation can comprise a distortion of the light pattern. The depth can be measured based on the distortion of the light pattern. The light pattern can be formed by a diffraction grating. The light pattern can comprise a plurality of dots. The depth can be measured by time-of-flight based on a phase shift between the projected and the reflected infrared radiation.

The target visualized can comprise a tissue excised from a subject organism. The tissue can comprise, for example, a precancerous tissue, a cancerous tissue, or both. The cancerous tissue can comprise a tumor. For example, the tumor can be a breast tumor and the excised tissue comprises a lumpectomy. The excised tissue can comprise a fluorescent molecule associated with a probe targeting a tumor receptor, an enzyme-activated fluorescent molecule, or a genetically modified oncolytic virus-induced fluorescence, or any combination thereof. For example, the tumor receptor can comprise HER2, a folate receptor, CXCR4, a hormone receptor, an EGFR, or a VEGF, or a combination thereof. Examples of hormone receptors include estrogen receptors and progesterone receptors. The enzyme can comprise, for example, a protease, a carbohydrase, a lipase, a transferase, an oxidoreductase, a matrix metalloprotease (MMP), a caspase, a cathepsin, a kallikrein, serine protease, isocitrate dehydrogenase, or an enzyme overexpressed by tumor cells, or a combination thereof. The target can comprise, for example, a surgical bed from which a tissue has been excised. The surgical bed and the excised tissue can comprise, for example, a cancerous tissue.

The method can further comprise one or more of the following steps. A three-dimensional white light image can be created from the two-dimensional white light image and the three-dimensional map. A three-dimensional fluorescence image can be created from the two-dimensional fluorescence image and the three-dimensional map. The three-dimensional white light image and the three-dimensional fluorescence image can be aligned using the one or more fiducial markers to form a three-dimensional superimposed image. The method can be performed at least twice, in either order, the two performances comprising a first performance and a second performance. The first performance can be performed on the target. The target can be a first target comprising an excised tissue. The second performance can be performed on a second target comprising a surgical bed from which the tissue is excised. The three-dimensional superimposed image of the first performance can be a first three-dimensional superimposed image. The three-dimensional superimposed image of the second performance can be a second three-dimensional superimposed image. The method can further comprise comparing the first and second three-dimensional superimposed images to determine a fluorescent continuity between the excised tissue and the surgical bed based on an orientation of the excised tissue relative to the surgical bed. The fluorescent continuity can comprise, for example, one or more of a bacterially infected tissue, a virally infected tissue, a burn, a precancerous tissue, a cancerous tissue, a connective tissue, a muscle tissue, a blood vesicle, and a skin feature. The fluorescent continuity can correspond to a compromised tissue. The method can further comprise excising at least a portion of the compromised tissue from the surgical bed.

The method can further comprise capturing a companion three-dimensional image of the target area and the one or more fiducial markers using an imaging technique comprising, for example, one or more of computerized tomography (CT), magnetic resonance imaging (MRI), photoacoustic imaging, ultrasound, and optical coherence tomography. The three-dimensional superimposed image, the superimposed image being a first three-dimensional superimposed image, can be superimposed with the companion three-dimensional image to form a second three-dimensional superimposed image. The capturing of the companion three-dimensional image can comprise a second set of one or more fiducial markers, the one or more fiducial markers comprising first and second sets of fiducial markers. The companion three-dimensional image can be captured using computerized tomography and the one or more fiducial markers can comprise at least one fluorescent molecule and at least one CT contrast agent. The companion three-dimensional image can, for example, be captured using photoacoustic imaging, and the target area comprises a breast tumor and an anti-HER2 dual fluorescence-photoacoustic probe.

In accordance with the present disclosure, an imaging device is provided. The imaging device can comprise one or more of the following components and/or characteristics, for example, a chamber, an imaging system, and a data output system. A chamber can comprise a door comprising an interior door wall. The chamber can comprise a sidewall, a floor, and a ceiling. A sample platform can be configured to support a sample during imaging. An imaging system can be positioned within the chamber. The imaging system can comprise, for example, a fluorescence imaging subsystem, a visible light imaging subsystem, an infrared measuring subsystem, and at least one image sensor configured to detect radiation. A data output system can be configured to receive the detected radiation and to output data associated with the detected radiation. The imaging device can be configured to perform any suitable imaging protocol, for example, the imaging device can be configured to perform any method described herein, portion thereof, or modification thereof.

The sample platform and the imaging system can be configured to move relative to one another to image the sample. The sample platform can rotate about a central axis. The imaging system rotates about a central axis. The sample platform and the imaging system can share a common axis of rotation or can have separate rotation axes.

The chamber in a closed position can provide a substantially opaque barrier to visible light exterior to the chamber. The imaging system can be associated with the chamber surface or set apart from the chamber surface using one or more supports. The sample platform can optically transparent. The sample platform can be sufficiently optically transparent to allow for imaging of a sample from below the sample platform. For example, one or more images can be captured of the sample before, during, or after rotation of the sample and/or an imaging system. The sample platform can be formed from any appropriate material or combination of materials. For example, the sample platform can be formed from a glass, a polymer, a ceramic, or any combination thereof.

The imaging system can be a first imaging system and the imaging device can further comprise a second imaging system. The first imaging system can be positioned to image the sample from above the sample platform and the second imaging system can be configured to image the sample from below the sample platform. The first imaging system can be associated with a first rotatable frame positioned above the sample platform. The second imaging system can be associated with a second rotatable frame located below the sample platform. The first rotatable frame can comprise an arm to which the fluorescence subsystem, the visible light subsystem, and the infrared subsystem of the first imaging system are attached. The second rotatable frame can comprise a disc to which the fluorescence subsystem, the visible light subsystem, and the infrared subsystem of the second imaging system are attached.

The fluorescence subsystem, the visible light subsystem, and the infrared subsystem can be separately controllable or controllable together in any combination. The fluorescence subsystem, the visible light subsystem, and the infrared subsystem can be configured to be activated in a predetermined sequence. The visible light subsystem can be configured to deactivate during activation of the fluorescence subsystem, the infrared subsystem, or both.

The sample platform can comprise an orientation marker for placement of the sample on the sample platform with respect to a coordinate system. Any number of kind of orientation marker can be used. For example, the orientation markers can be raised and/or flush with the sample platform. The orientation markers can be placed in any suitable locations on the sample platform. For example, the orientation markers can be place about a perimeter of the sample platform. A sample can be oriented in the box so that anterior, superior, lateral, medial posterior and/or inferior margins are located in a desired location on the sample platform.

The sample platform can have any appropriate shape. For example, the sample platform can be substantially circular. The sample platform can have raised sides and/or one or more channels to control fluid runoff from a sample. The sample platform can comprise a fiducial marker. The sample platform can comprise a plurality of fiducial markers. Fiducial markers on the sample platform can complement or replace one or more fiducial markers on the sample itself.

The imaging device can comprise a completion indicator configured to indicate that imaging of a sample is complete. The completion indicator can comprise an audible signal, a visible signal, or both. The imaging device can comprise a door lock. The door lock can be manual, programmable, or automatic. The door lock can be configured to engage during sample imaging and disengage upon completion of sample imaging. The door and/or any other part of a housing forming the chamber can have a transparency. The transparency can be controllable. The transparency can be adjustable to be substantially opaque during sample imaging. The door and/or any other part of the housing can comprise a window. The window can be controllable to be substantially opaque during sample imaging.

The imaging device can comprise a user interface, can be operatively associated with the user interface, or both. Any appropriate number, type, or combination of user interfaces can be employed. The user interface can be on, near, or at a distance from the imaging device. The user interface can be located in any convenient location on the user device. The user interface can permit a user to control a function of the imaging device. The function can comprise any number, type, or combination of functions. For example, the function can comprise selection of an imaging program, programming of an imaging cycle, imaging timer, door unlock, door lock, door transparency, data selection, data output, data display, data processing, temperature, sample identification, fluorophore identification, power control, password entry, or rotation speed, or any combination thereof.

The fluorescence subsystem can comprise, for example, the following components. An excitation light source can be configured to emit a first radiation capable of exciting a fluorophore. A filter can be configured to prevent passage of reflected excitation light and permit passage of fluorescence emitted by the fluorophore. An imaging lens can be provided to focus or otherwise manipulate radiation. The visible light subsystem can comprise a visible light source configured to emit a second radiation. The second radiation can comprise white light. The second radiation can comprise monochromatic visible light. The infrared subsystem can comprise an infrared light source configured to emit a third radiation. The third radiation can comprise infrared radiation. The infrared radiation can comprise near infrared radiation.

The at least one image sensor can be configured to detect radiation comprising the fluorescence, reflected visible light, and reflected infrared light. The at least one sensor can comprise any number or type of sensor. For example, the at least one sensor can comprise at least two sensors. The at least two sensors can comprise a first sensor configured to detect fluorescence and a second detector configured to detect reflected visible light. The at least one sensor can comprise at least three sensors comprising a first sensor configured to detect fluorescence, a second detector configured to detect the reflected visible light, and a third sensor configured to detect reflected infrared light.

The imaging device can comprise a common radiation source configured to operate with one or more of the light sources. The one or more light sources can comprise a converter to convert source radiation emitted from the common radiation source to the first radiation, the second radiation, or the third radiation, or a combination thereof. The converter can comprise, for example, a filter, a lens, a prism, a diffractor, or a quantum dot, or a combination thereof. The excitation light source can comprise a first converter, the visible light source can comprise a second converter, and the infrared light source can comprise a third converter.

The imaging device can comprise a display unit. The display unit can be configured to display the data output by the data output system. The data comprises a two-dimensional image, a three-dimensional image, or both. The display unit can be configured to display data generated by the imaging device, data generated by a different imaging device, or both. The data displayed can, for example, comprise histology data. A tumor can be characterized or detected based on its fluorescence contrast (for example, intensity, color, hue, luminance, or the like), for example, after 405 nm excitation, this data can be depicted graphically on a three-dimensional image rendering of the specimen viewed on the display unit. The display unit can comprise a touchscreen. The touchscreen can replace or complement a user interface for the imaging device.

The detected radiation can comprise, for example, one or more of fluorescence, reflected visible light, and reflected infrared light. The detected radiation can comprise fluorescence, reflected visible light, and reflected infrared light. The imaging device can be configured to visualize a target area of the sample. The imaging device can comprise a processor and/or can be operatively associated with a processor. The processor can be configured to generate a three-dimensional map of the sample or a target area thereof. The three-dimensional map can be generated from infrared light reflected from the target area. The processor can be further configured to capture a two-dimensional visible light image of the target area based on the detected radiation. The processor can be configured to create a three-dimensional visible light image of the target area based on the three-dimensional map and the two-dimensional visible light image. The processor can be configured to capture a two-dimensional fluorescence image of the target area based on the detected radiation. The processor can be configured to create a three-dimensional fluorescence image of the target area based on the three-dimensional map and the two-dimensional fluorescence image. The processor can be further configured to align a three-dimensional visible light image of the target area with a three-dimensional fluorescence image of the target area to form a three-dimensional superimposed image of the target area. The alignment can be performed based on co-registration of one or more fiducial markers associated with the target area.

The imaging device can comprise at least one power source or be associated with at least one power source. For example, the power source can comprise an internal power source, an external power source input, a power adapter, or any combination thereof. The power source can comprise a battery, an outlet-accessed line source, or both.

One or both of the imaging system and the sample platform can be rotatable about a central axis. The imaging device can comprise a motor configured to rotate one or both of the imaging system and the sample platform. The motor can comprise a first motor configured to rotate the imaging system and a second motor configured to rotate the sample platform. One or both of the imaging system and the sample platform can be rotatable at a continuous speed, a variable speed, continuously, intermittently, or reversibly, or a combination thereof. For example, one or both of the imaging system and the sample platform can be rotatable at a speed from about 0.01 rpm to about 1,000 rpm, from about 1.0 rpm to about 100 rpm, or from about 5.0 rpm to about 50 rpm, or any intervening speed or range thereof, or a combination thereof. The sample platform can further comprise a sample restraint configured to maintain the sample in a fixed position relative to the sample platform during imaging.

The imaging device can be configured for ease of cleaning and sterilization. For example, the sample platform, chamber surface, or both can be coated with an antimicrobial agent. The imaging device can comprise a sanitization system. For example, the sanitization system can comprise an autoclave function.

The data output system can have any desired set of functions. For example, the data output system can comprise a cable, a cable port, or both configured to operably connect the imaging device to an external device, information network, or both. The imaging device can comprise and/or be in communication with a data storage. The data storage can be in communication with the data output system. The data storage can be configured to store data output by the data output system. The data storage can be integral with, removable from, or remote from the imaging device. The data output system can be in wired or wireless communication with a data storage, external device, and/or network.

The imaging device can be of any suitable shape, size, and/or overall dimensions. For example, the imaging device can be configured to be placed on a benchtop. The benchtop can be, for example, a benchtop located in a pathology or other diagnostics laboratory. The benchtop can be located in or adjacent a surgical ward. The imaging device can comprise a leveling unit to permit level placement on a benchtop. For example, the leveling unit can comprise one or more adjustable legs.

Figure 5A:
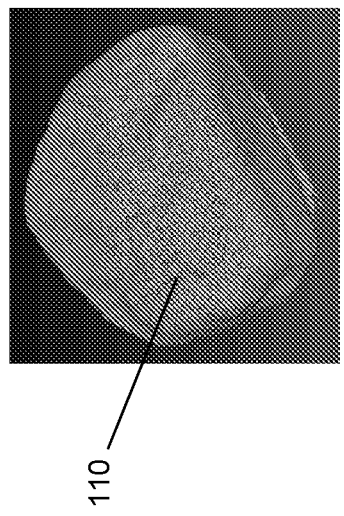
FIG. 5 is a perspective view of an embodiment of an imaging device of the present disclosure in an open configuration.
Figure 5B:
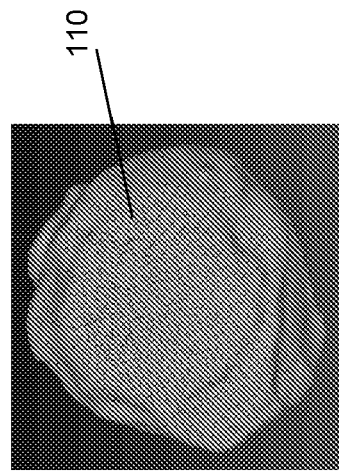

Examples of non-limiting embodiments are described with reference to the figures as follows. FIG. 5 is a perspective view of an embodiment of a first imaging device 210 of the present disclosure in an open configuration. First imaging device comprises a housing 212 including a door 214. Door 214 is shown in cutaway form and has a door interior surface 216. Door 214 is shown set in housing first surface 218, but can be elsewhere located. Housing top surface 220 is depicted with a user interface 222, but user interface 222 can be located elsewhere. Through cutaways in housing lateral surface 224, a power adaptor 226, and a data output unit (system) 228 are visible. The location of these and other components can be varied.

Housing 212 can surround or partially surround a chamber 230. Chamber 230 includes sidewalls 232, a floor 234, and a ceiling 238. Chamber 230 is configured to accept a sample 250 for imaging. Chamber 230 contains a sample platform 252 configured to accept sample 250. Arrows indicate that sample platform 252 can rotate in either direction. Sample platform 252 can be configured to rotate about a central axis 254.

A first fixed frame 256 is attached to the chamber in the form of a first fixed frame first fixture 258 and a first fixed frame second fixture 260, which are configured to mount components of an imaging system including subsystems and components thereof. Mounted to first fixed frame first fixture 258 are an upper excitation source 270, an upper visible light source 272, and an upper sensor 276. An upper filter 278 is associated with an upper sensor 276. Mounted to first fixed frame second fixture 260 are another upper visible light source 272 and an upper infrared source 274. The number of mounted components and their placement can be varied. The number and arrangement shown in FIG. 5 is an example.

Figure 6A:
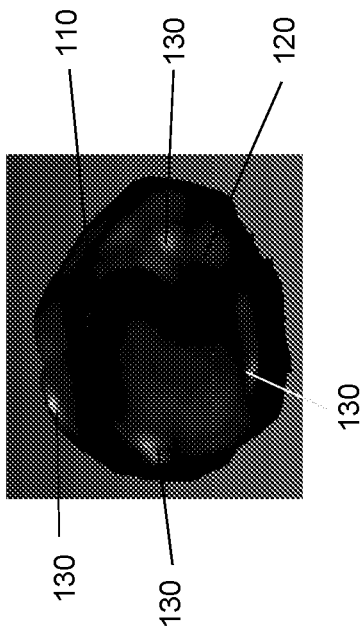
FIG. 6 is a front view of the imaging device shown in FIG. 5.
Figure 6B:
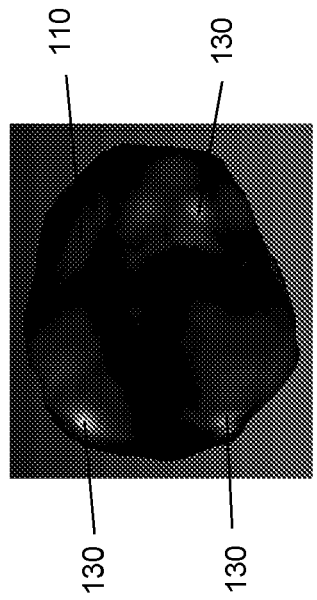

FIG. 6 is a front view of the imaging device shown in FIG. 5. Through a cutaway (although they could be seen through a transparent embodiment) of sample platform 252, a second fixed frame 280 is visible located about a motor 282. Motor 282 can be configured to rotate sample platform 252. Mounted on second fixed frame 280 are a lower excitation source 290, a lower visible light source 292, a lower infrared source 294, and a lower sensor 296. A lower filter 298 is depicted associated with lower sensor 296. The number of mounted components and their placement can be varied. The number and arrangement shown in FIG. 6 is an example.

Figure 7A:
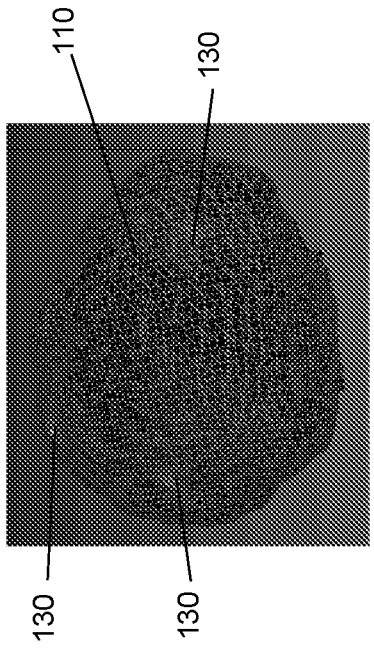
FIG. 7 is a top view of the imaging device shown in FIG. 5.
Figure 7B:
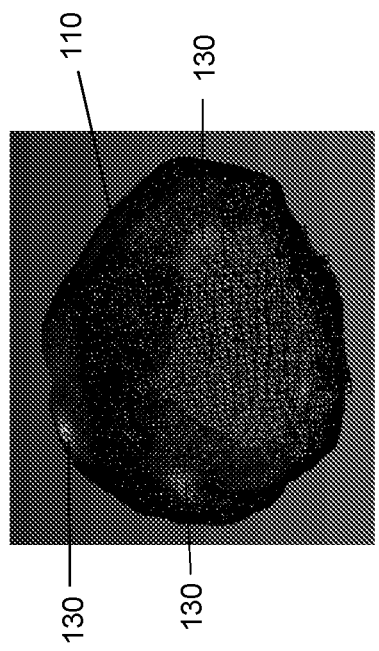

FIG. 7 is a top view of the imaging device shown in FIG. 5 and depicts an example of user interface 222 on housing top surface 220. A display 320 can include a touchscreen 322. A speaker 330 is located adjacent display 320 and can be configured to emit, for example, a sound associated with completion of an imaging scan cycle. A plurality of indicators 340 are also depicted. The indicators can comprise, for example, a light indicating that the associated function is active or inactive. The indicator can also comprise a button or other actuator that can complement or replace a corresponding interface on touchscreen 322 or elsewhere. A power switch 346 permits a user to turn the imaging device on and off. An on indicator 348 indicates that the imaging device is on and powered. Door release 350 permits a user to open door 214. Through a cutaway in housing upper surface 220, an engageable door lock 352 is visible. Open indicator 354 indicates that the door is open. Closed indicator 356 indicates that the door is closed and optionally that the door is also locked. A ready indicator 362 indicates that the imaging device is ready to start imaging a sample. A clean indicator 364 can indicate that a cleaning cycle is in progress or complete. A standby indicator 366 indicates that the imaging device has entered a standby mode, for example, for power saving purposes. An in-use indicator 368 indicates that the imaging device is in use. A done indicator 370 indicates that an imaging of a sample is complete. A scan indicator 372 indicates that an imaging cycle is in progress. An IR indicator 374 indicates that an infrared mode of an imaging cycle is active. A white light indicator 376 indicates that a white light or other visible light mode of an imaging cycle is active. A fluorescence indicator 378 indicates that a fluorescence mode of an imaging cycle is active. The arrangement, identity, and number of indicators and other components of user interface 222 can be varied, and can be alternatively or additionally located on other surfaces of the imaging device. That shown in FIG. 7 is only an example.

Figure 8A:
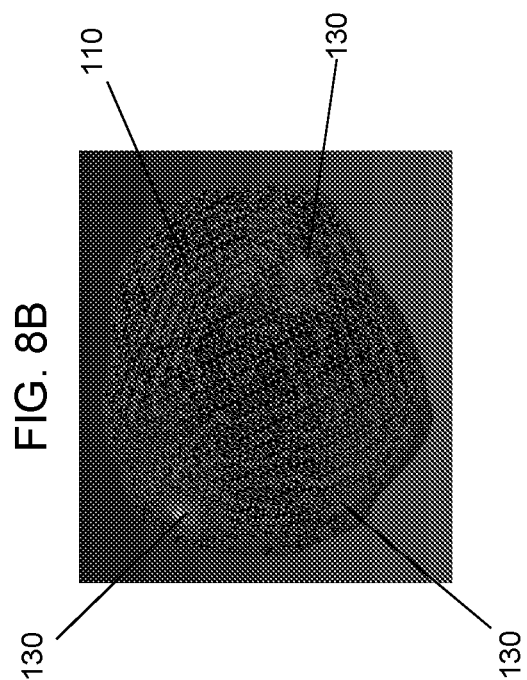
FIG. 8 is a back view of the imaging device shown in FIG. 5.
Figure 8B:
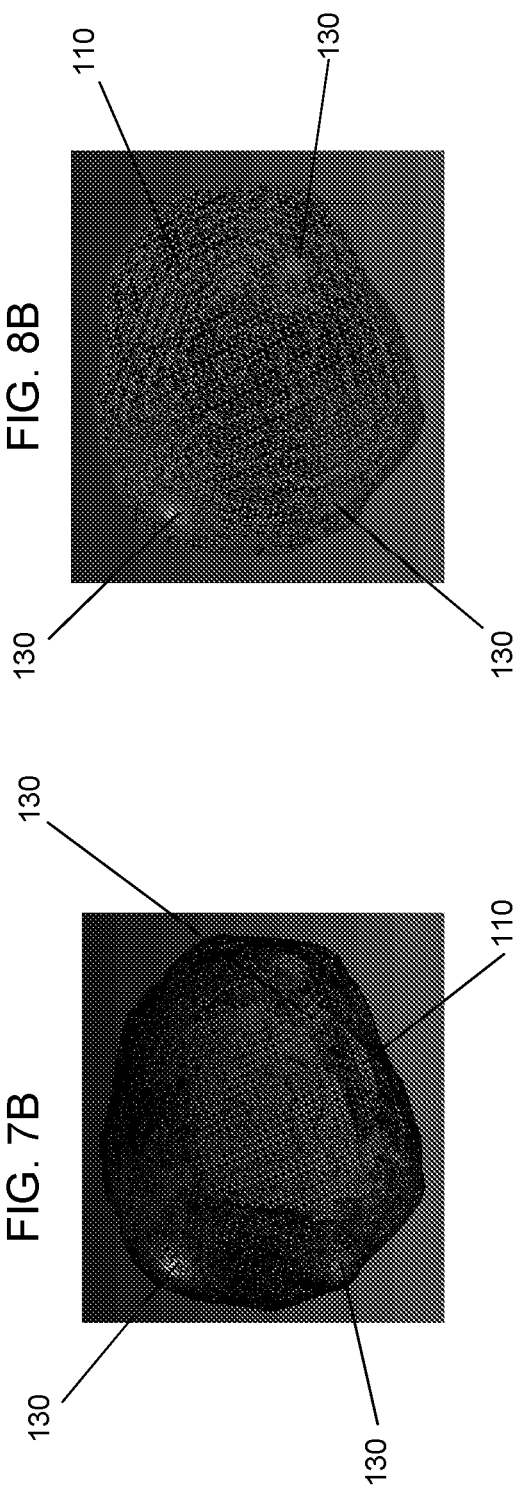

FIG. 8 is a back view of the imaging device shown in FIG. 5 from which housing back surface 390 is visible. A power cable 392 extends from housing back surface 390, which can be operatively associated with power adaptor 226 and a line source of electricity. First data port 394 and second data port 396 are set in housing back surface 390. First and second data ports 394, 396 can be in communication with data output unit 228. First and second data ports 394, 396 can be configured to accept data cables for connecting the imaging device to one or more external devices and/or networks. A video port 398 is set in housing back surface unit 390 and can be configured to accept a video cable for linking the imaging device to an external display. The arrangement, identity, and number of the component shown on housing back surface 390 can be varied, and can be alternatively or additionally located on other surfaces of the imaging device.

Figure 9A:
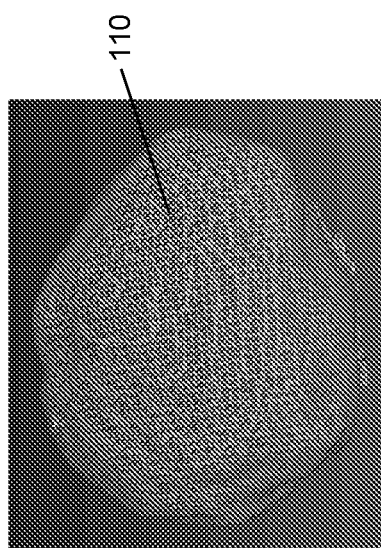
FIG. 9 is a perspective view of an embodiment of an imaging device of the present disclosure in an open configuration.
Figure 9B:
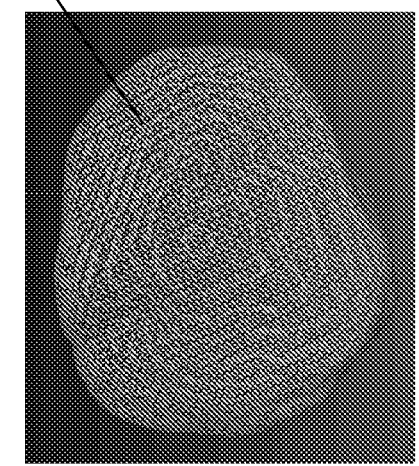

FIG. 9 is a perspective view of an embodiment of a second imaging device 410 of the present disclosure in an open configuration. Components and functionalities of second imaging device 410 can be the same as, similar to, or different from those of first imaging device 210. Mounted to a first rotatable frame 456 are an upper excitation source 270, an upper infrared source 274, an upper visible light source 272, and an upper sensor 276. An upper filter 278 is associated with an upper sensor 276. Through a cutaway (although they could be seen through a transparent embodiment) of sample platform 252, a second rotatable frame 480 is visible located about a motor 282. Motor 282 can be configured to rotate second rotatable frame 480. Mounted on second rotatable frame 480 are a lower excitation source 290, a lower visible light source 292, a lower infrared source 294, and a lower sensor 296. A lower filter 298 is depicted associated with lower sensor 296. Arrows indicate that first and second rotatable frames 456, 480 can rotate in either direction. The number of mounted components and their placement can be varied. The number and arrangement shown in FIG. 9 is an example.

Figure 10A:
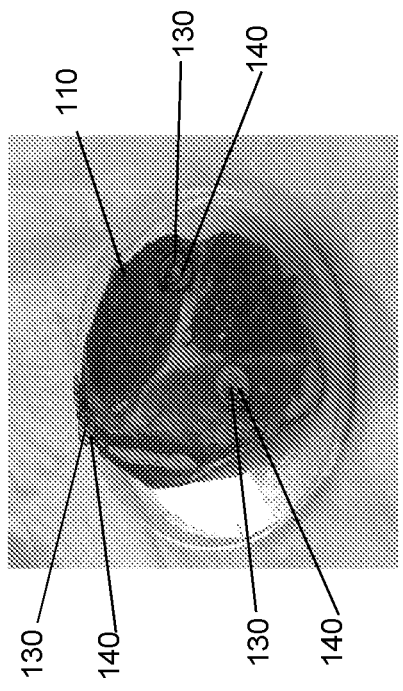
FIG. 10 is a front view of the imaging device shown in FIG. 9.
Figure 10B:
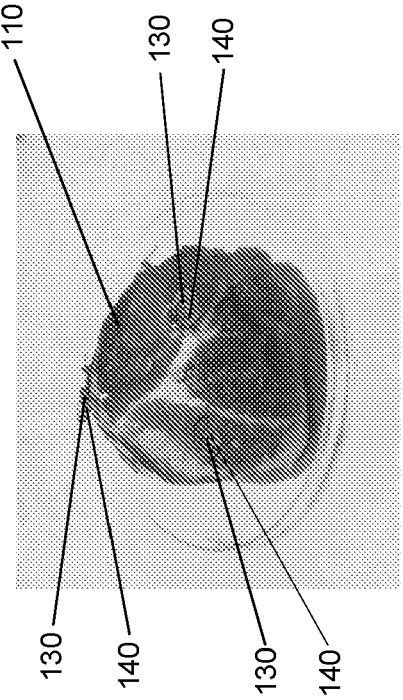

FIG. 10 is a front view of the imaging device shown in FIG. 9. A second motor 482 is visible in a cutaway of first rotatable frame 480. Second motor 482 can be configured to rotate first rotatable frame 480. The number of mounted components and their placement can be varied. The number and arrangement shown in FIG. 10 is an example.

Figure 11C:
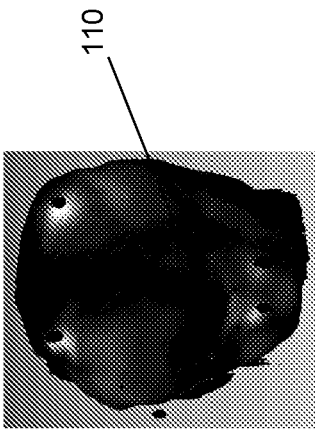
FIG. 11 is a perspective view of an embodiment of an imaging device of the present disclosure in an open configuration.
Figure 11B:
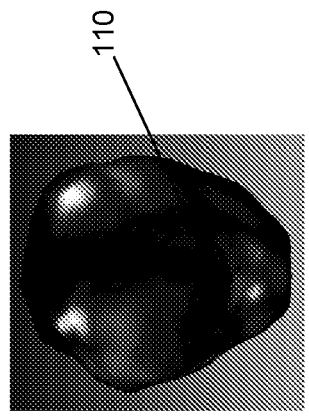
Figure 11A:
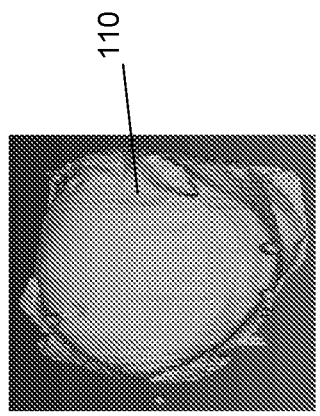

FIG. 11 is a perspective view of an embodiment of a third imaging device 510 of the present disclosure in an open configuration. Components and functionalities of second imaging device 510 can be the same as, similar to, or different from those of first imaging device 210. Mounted to an actuatable arm frame 556 towards a proximal end are an upper excitation source 270, an upper visible light source 272, and an upper sensor 276. An upper filter 278 is associated with an upper sensor 276. Mounted towards a distal end of actuatable arm frame 556 are another upper visible light source 272 and an upper infrared source 274. Actuatable arm frame 556 extends from arm base 558. Through a cutaway in arm base 558, a third motor 582, configured to move actuatable arm frame 556, is visible. The number of mounted components and their placement can be varied. The number and arrangement shown in FIG. 11 is an example.

Figure 12C:
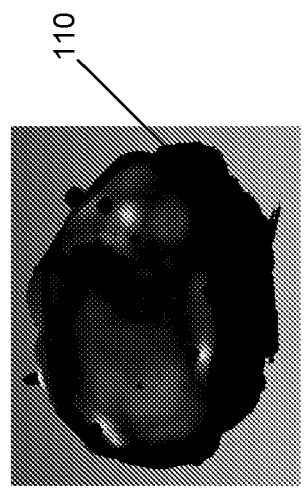
FIG. 12 is a perspective view of an embodiment of an imaging device of the present disclosure in a closed configuration.
Figure 12B:
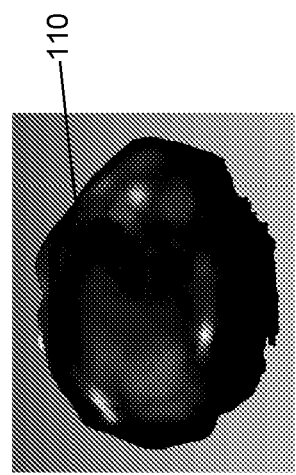
Figure 12A:
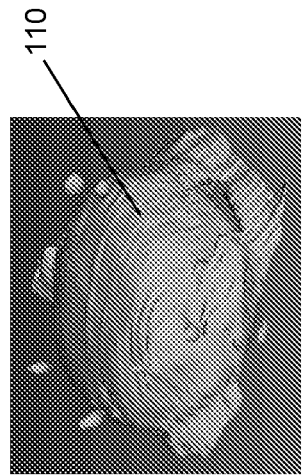
Figure 15B:
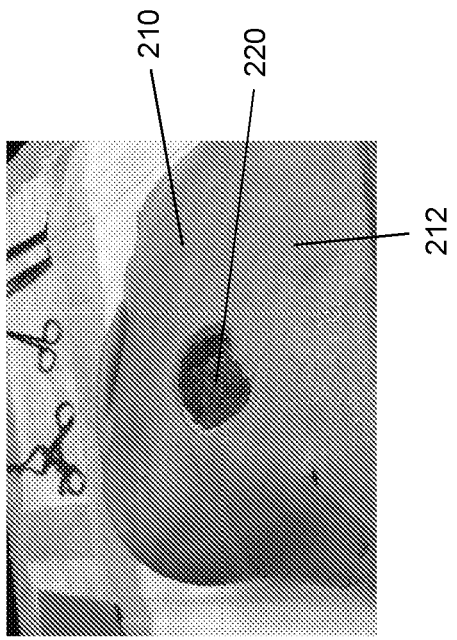
Figure 15A:
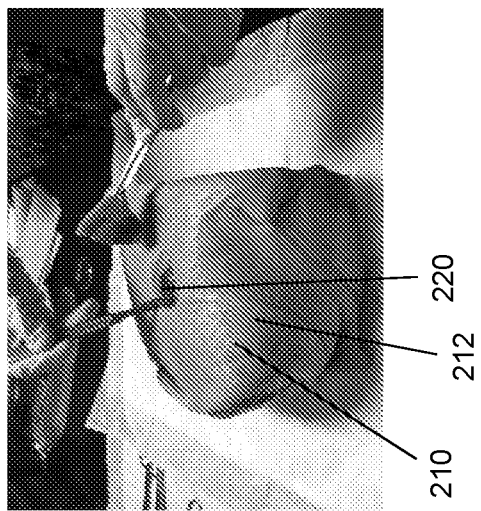
Figure 16:
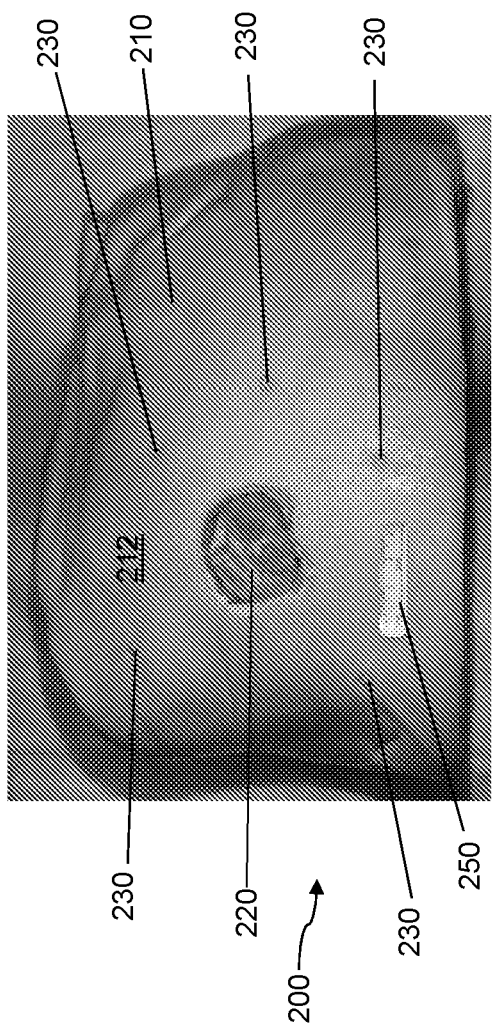
Figure 17B:
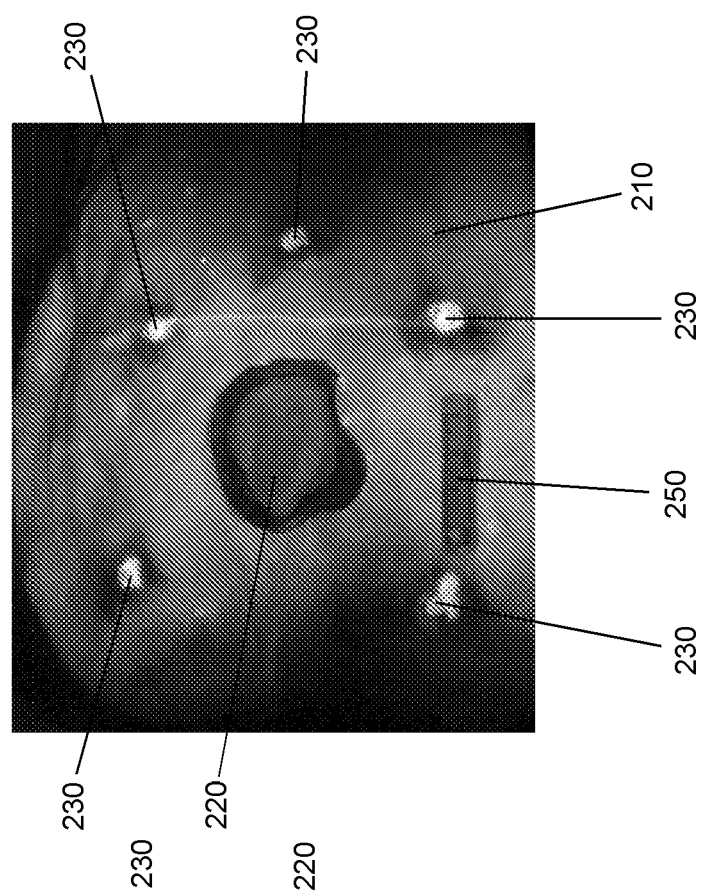
Figure 17A:
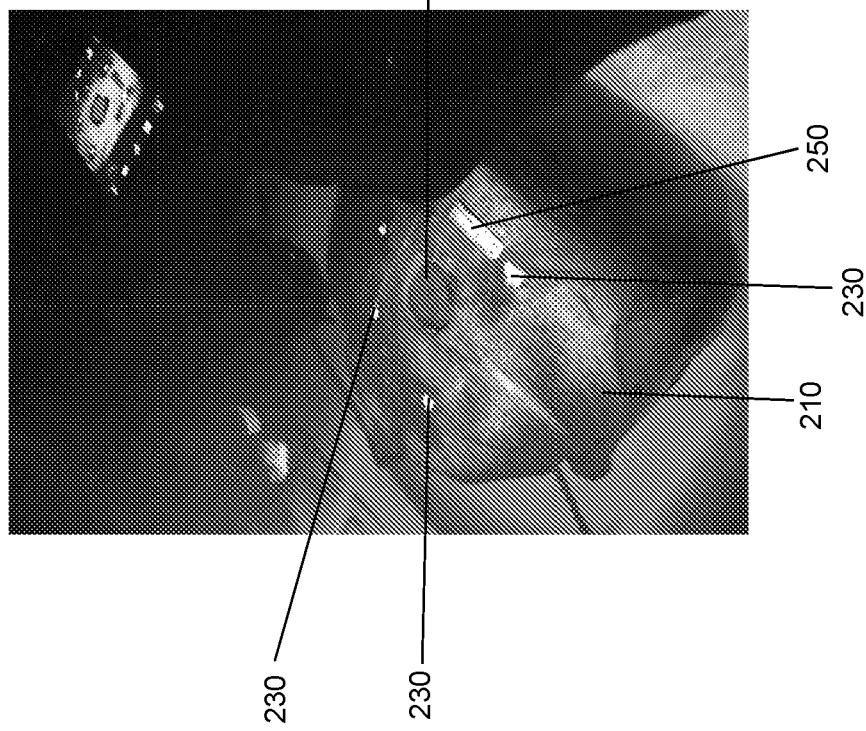
Figure 18A:
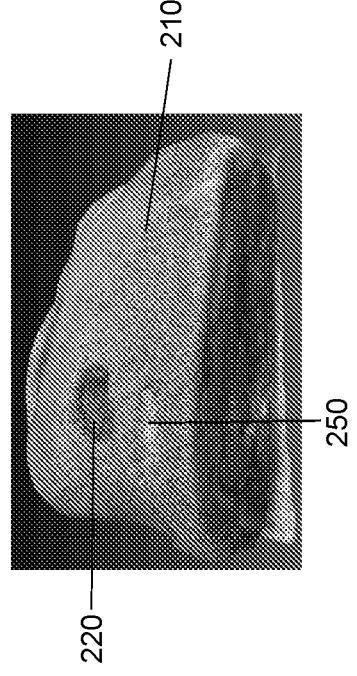
Figure 18B:
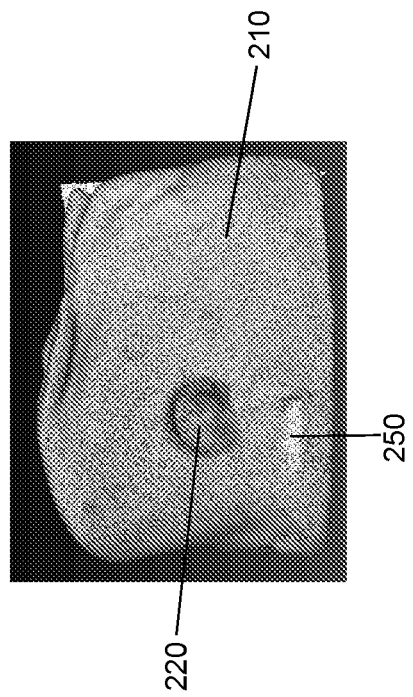
Figure 19A:
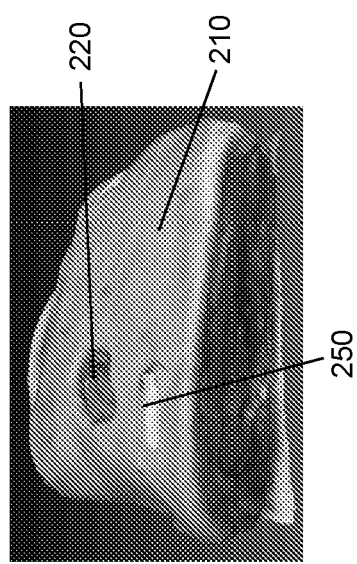
Figure 19B:
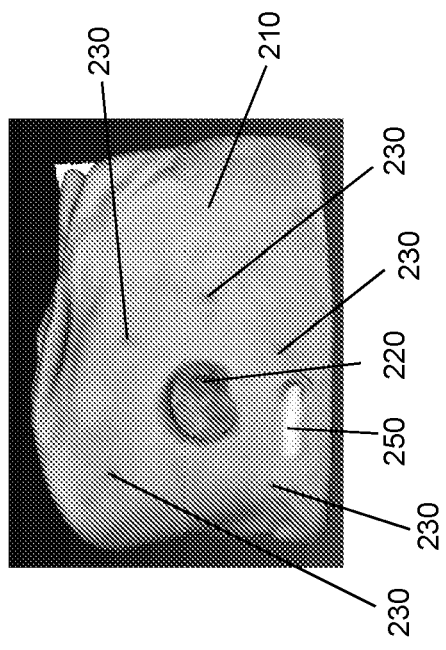
Figure 21A:
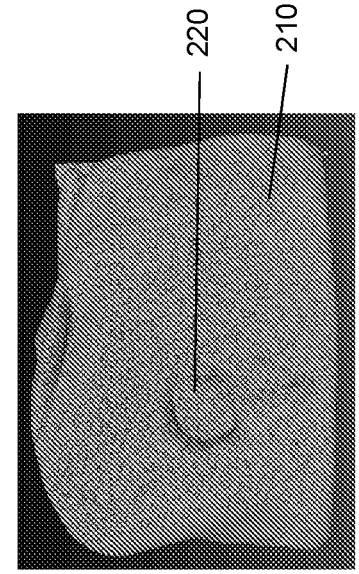
Figure 21B:
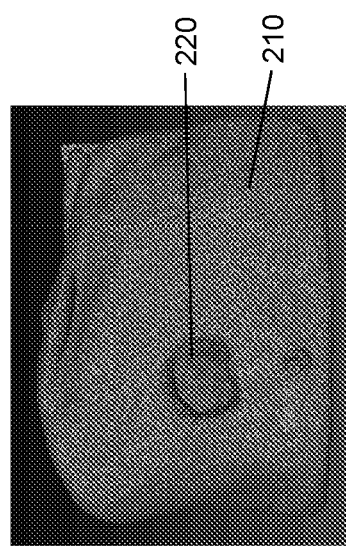
Figure 20A:
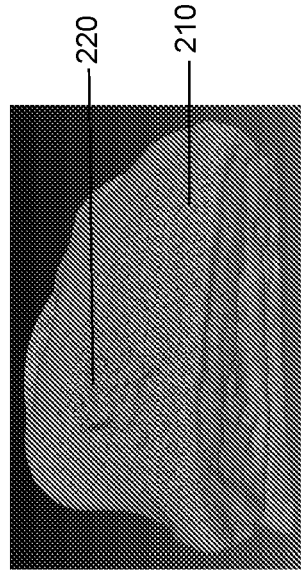
Figure 20B:
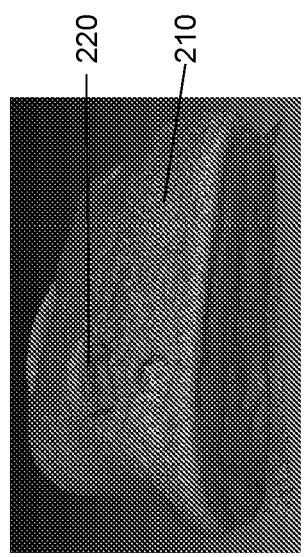
Figure 23A:
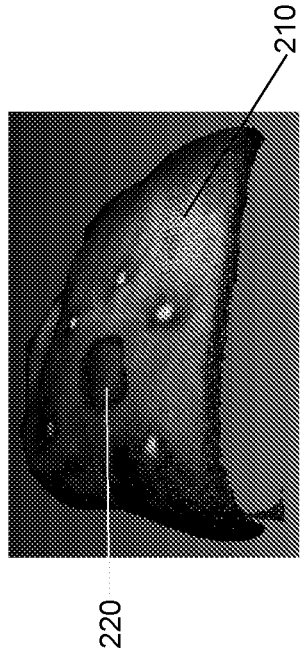
Figure 23B:
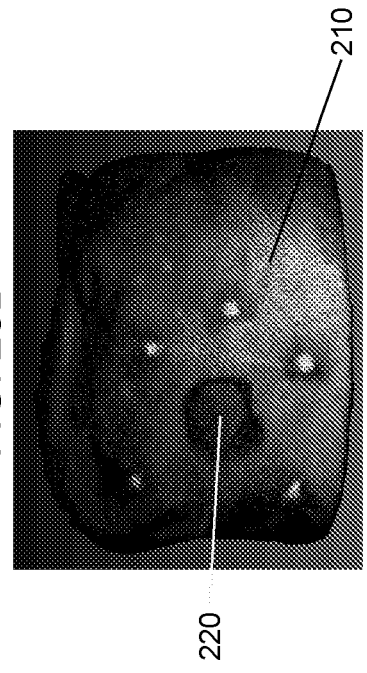
Figure 22A:
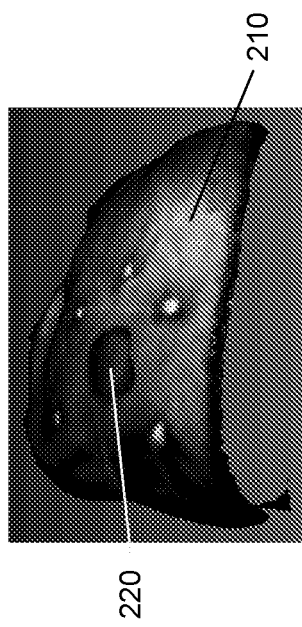
Figure 22B:
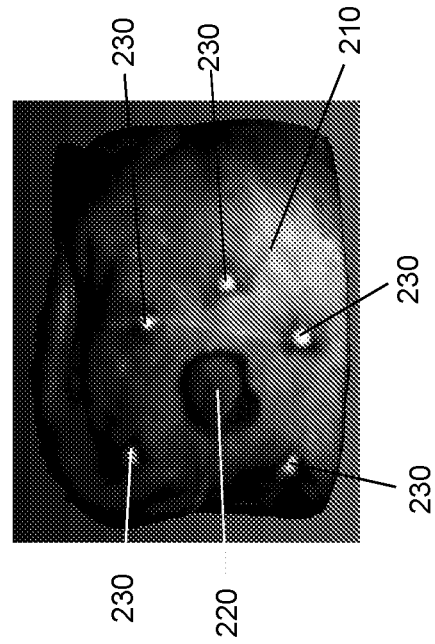
Figure 25A:
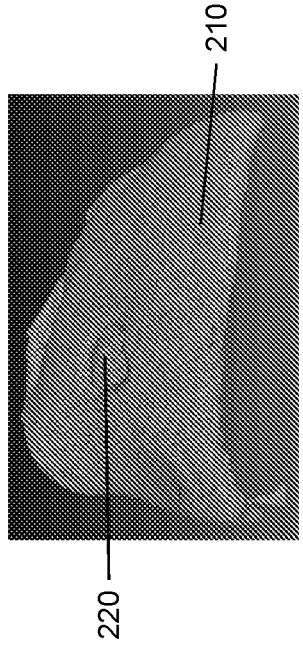
Figure 25B:
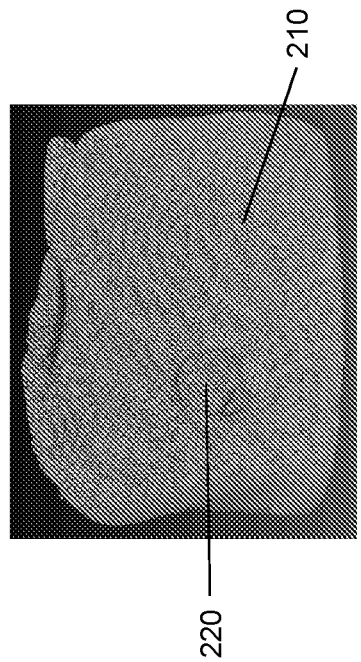
Figure 24A:
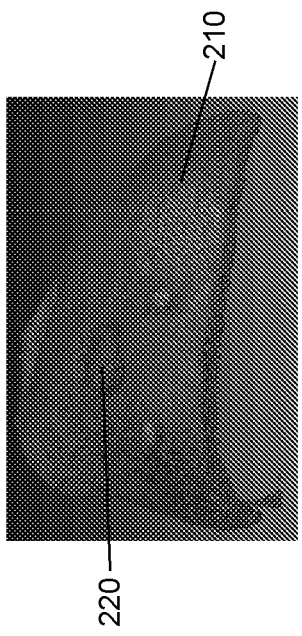
Figure 24B:
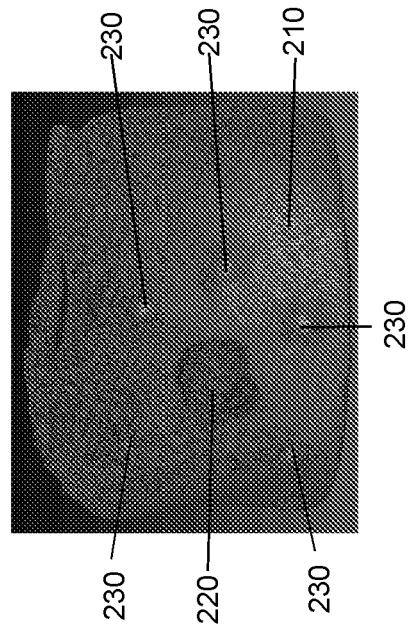
Figure 26B:
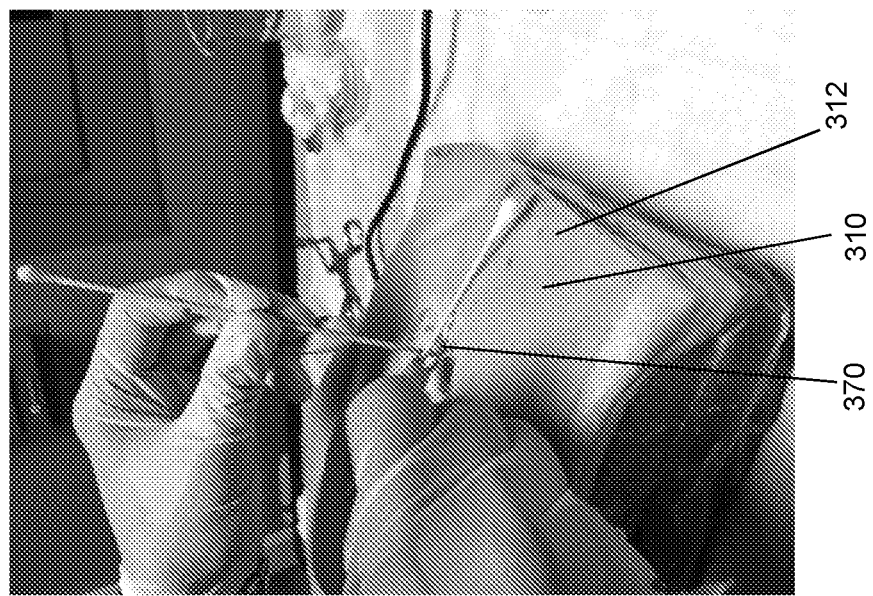
Figure 26A:
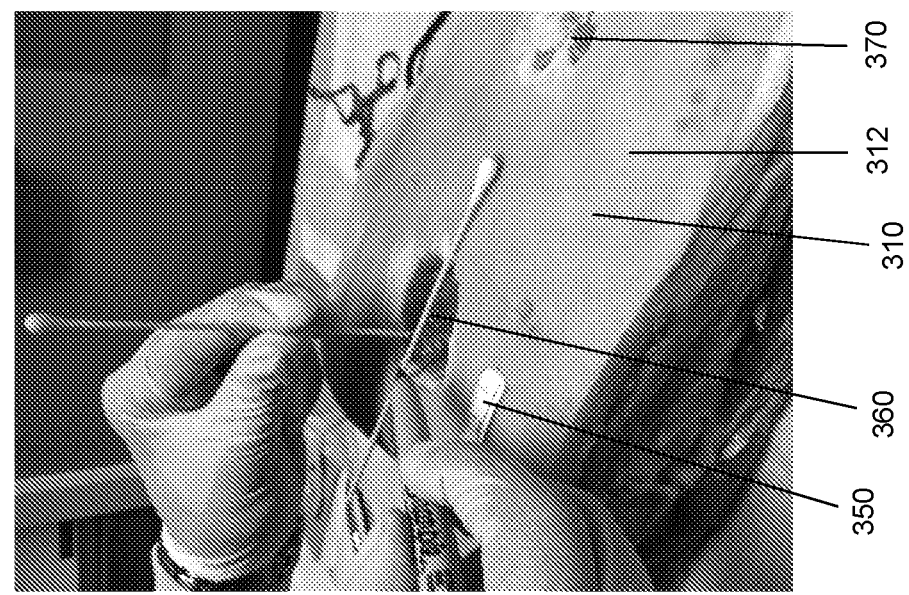
Figure 26D:
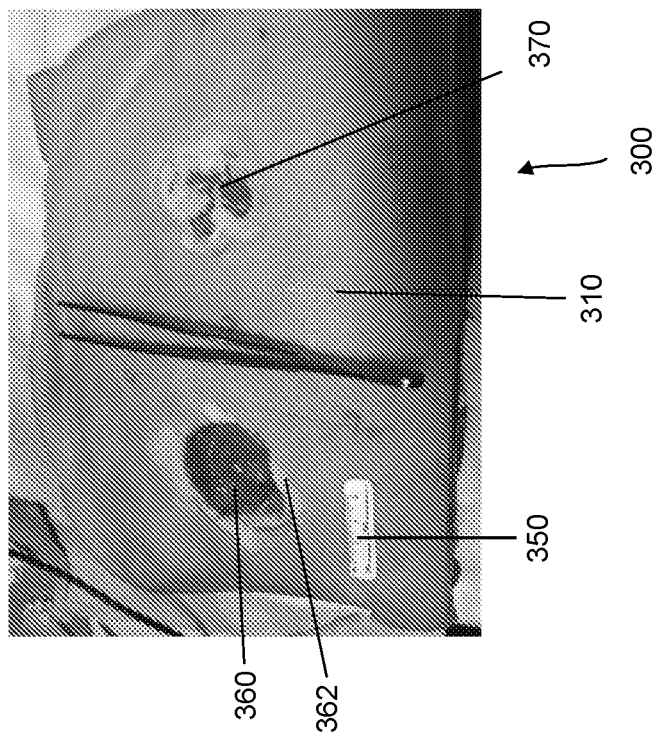
Figure 26C:
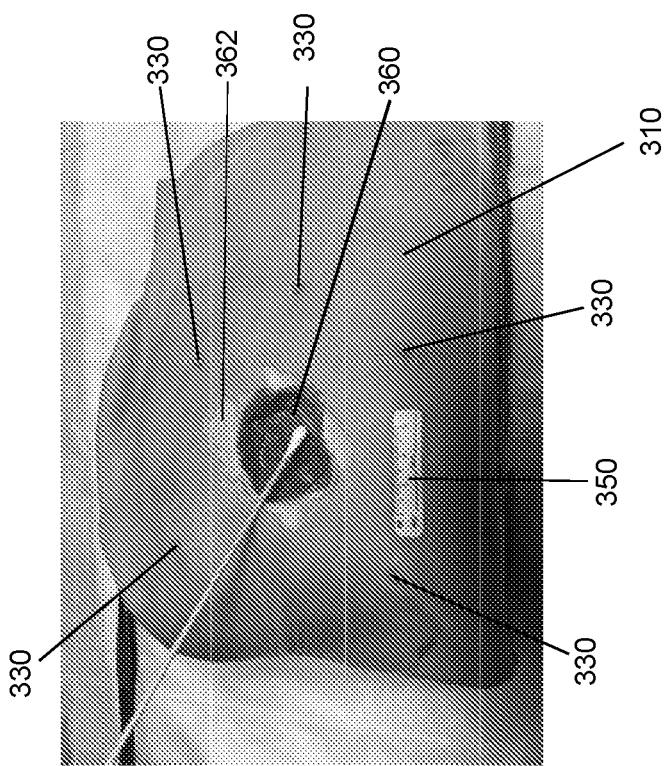
Figure 27A:
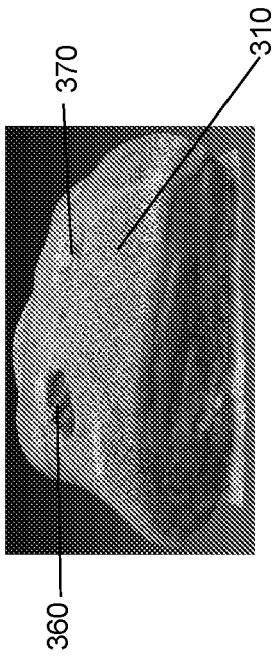
Figure 27B:
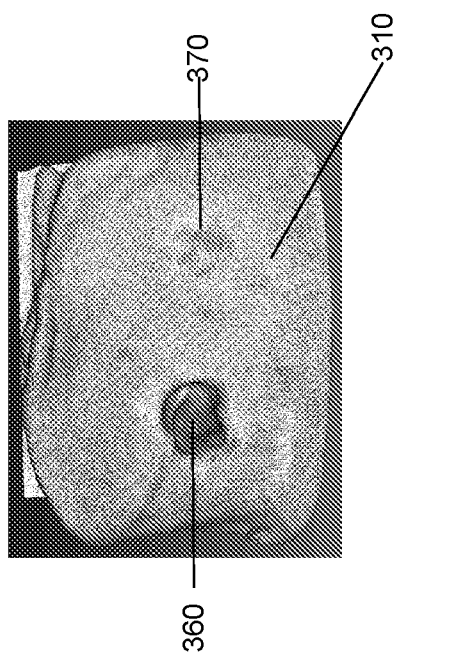
Figure 28A:
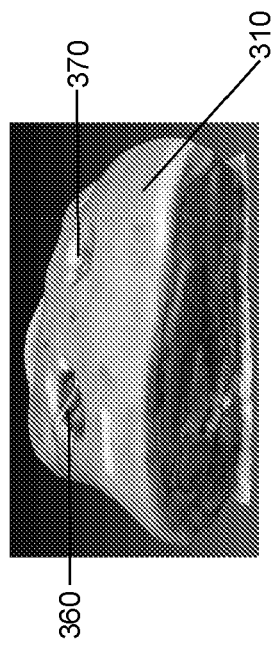
Figure 28B:
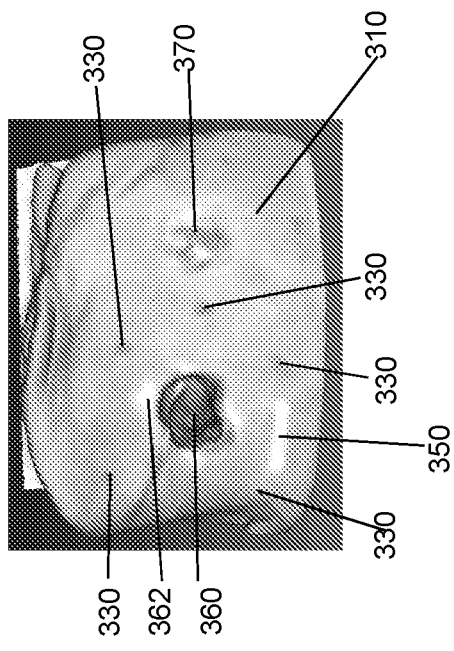
Figure 29A:
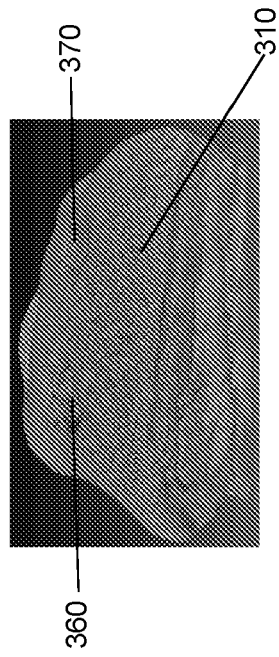
Figure 29B:
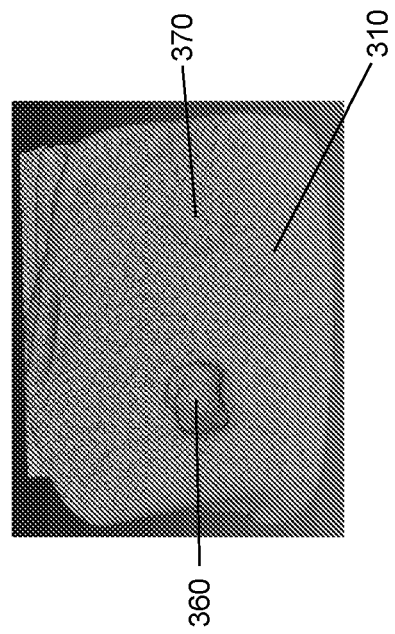
Figure 30A:
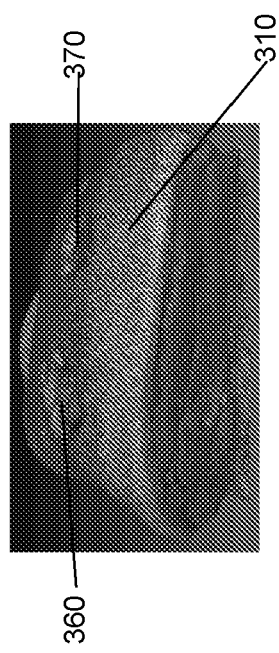
Figure 30B:
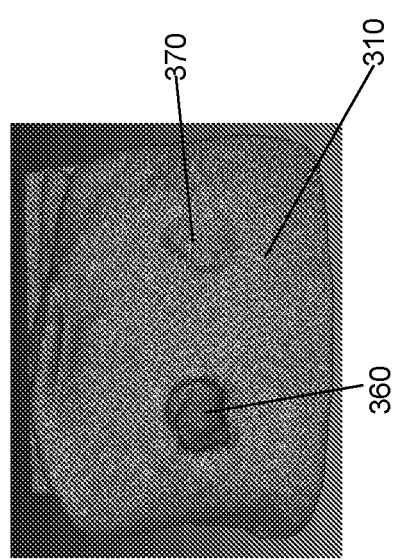
Figure 31A:
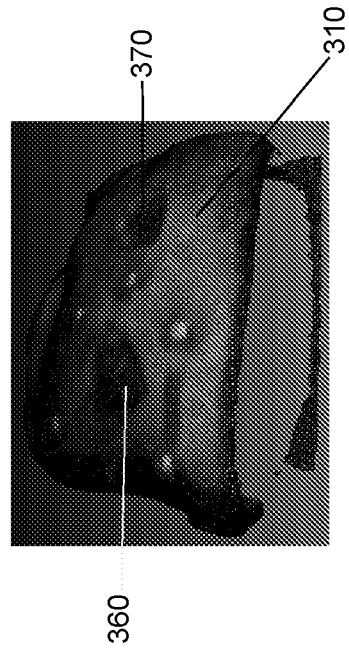
Figure 31B:
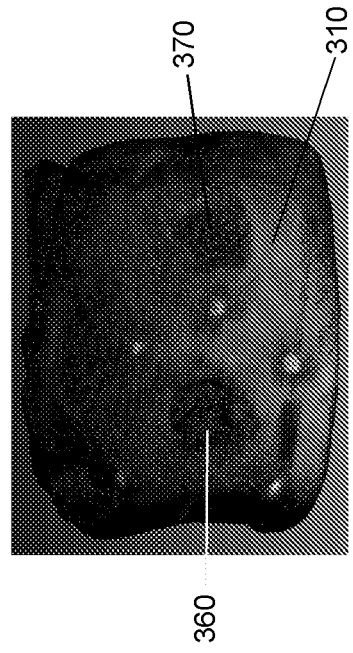
Figure 32A:
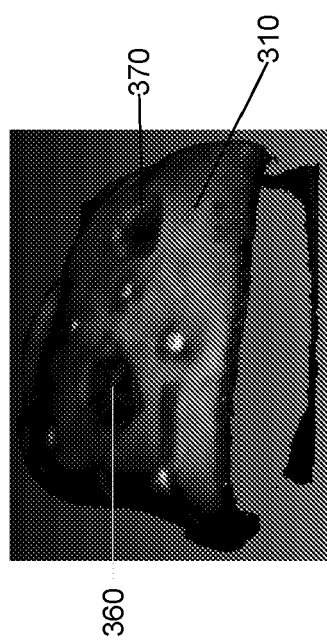
Figure 32B:
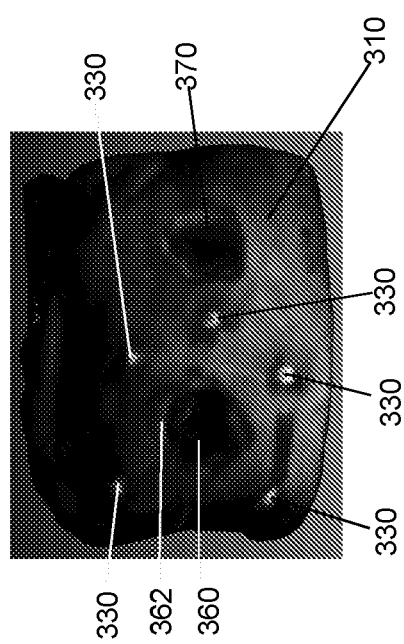
Figure 33A:
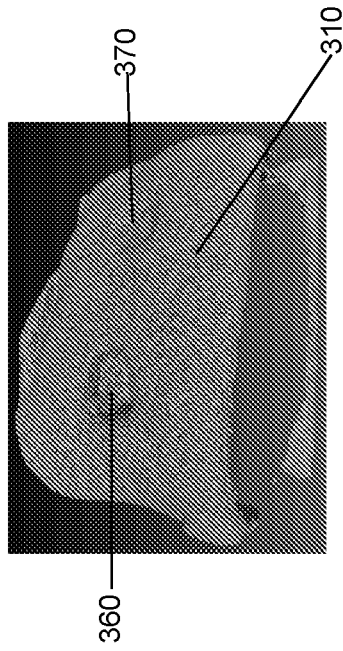
Figure 33B:
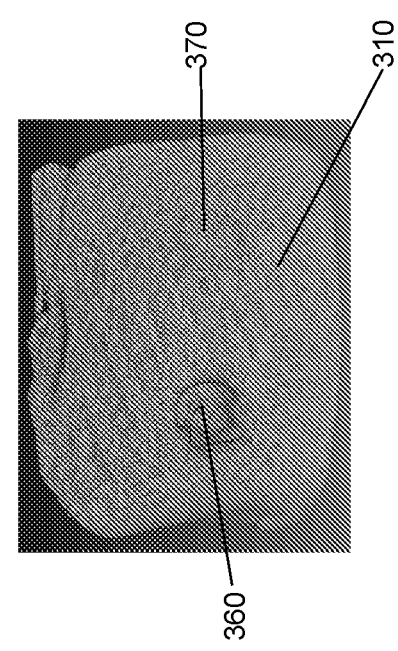
Figure 34A:
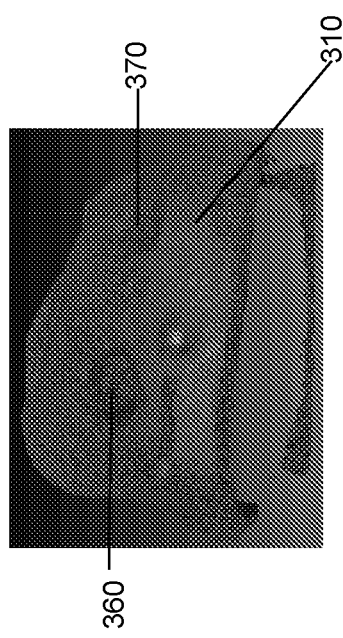
Figure 34B:
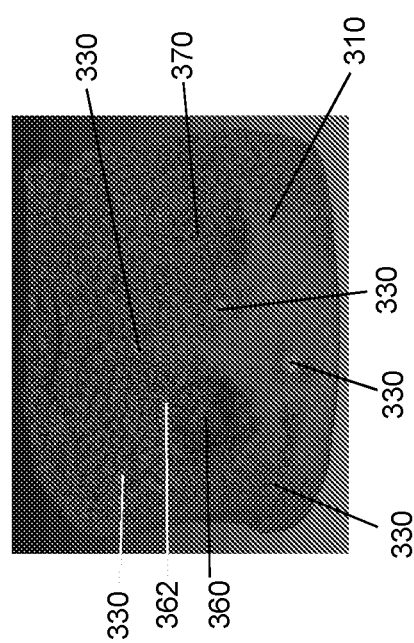
Figure 35B:
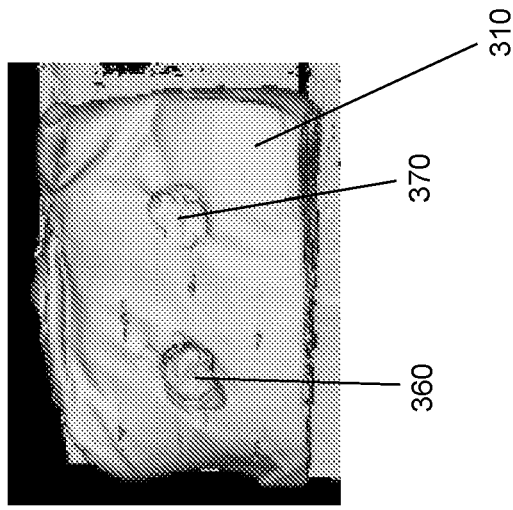
Figure 35A:
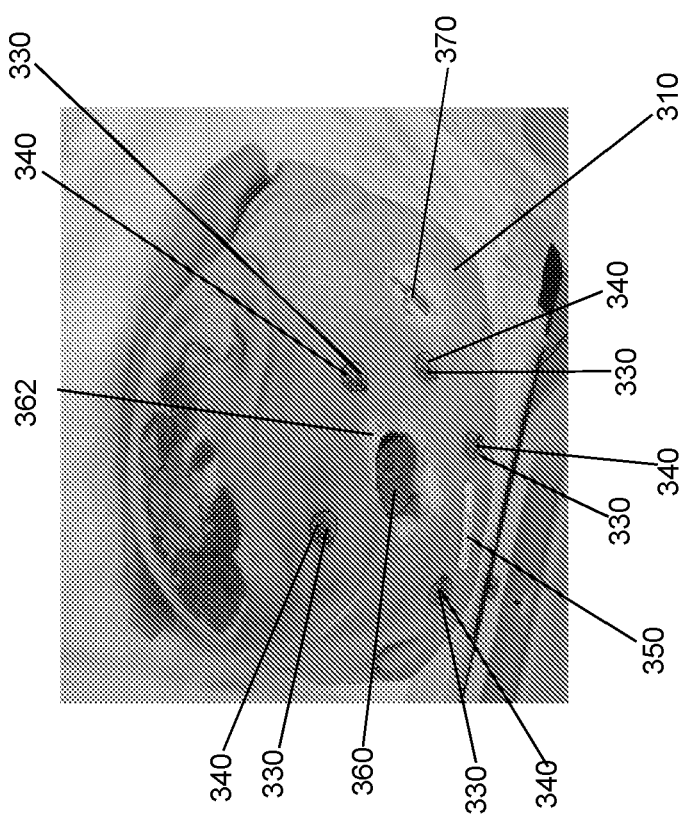
Figure 36A:
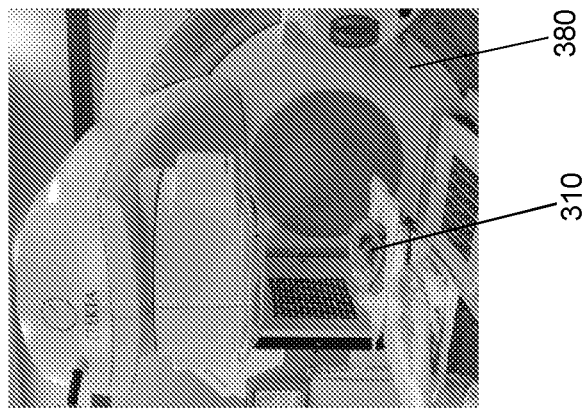
Figure 35D:
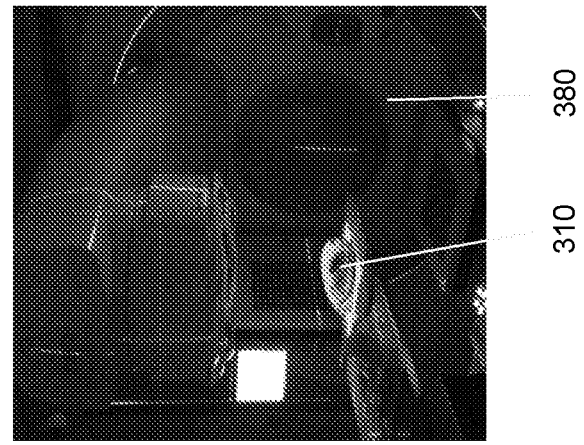
Figure 35C:
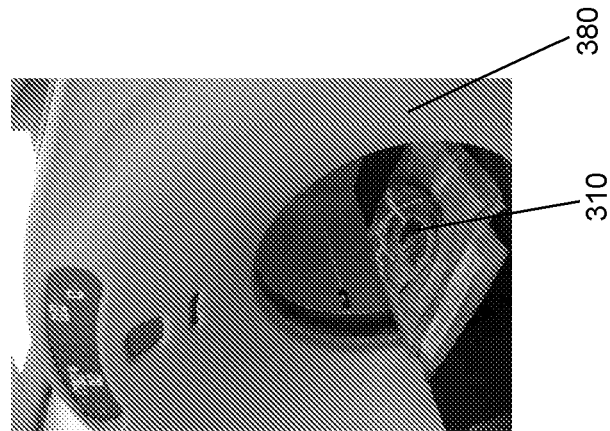
Figure 37:
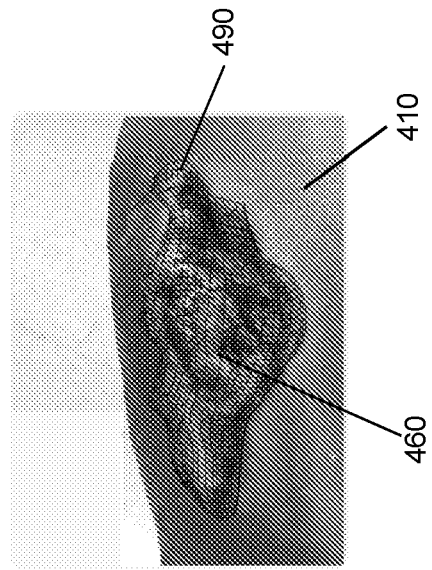
Figure 36B:
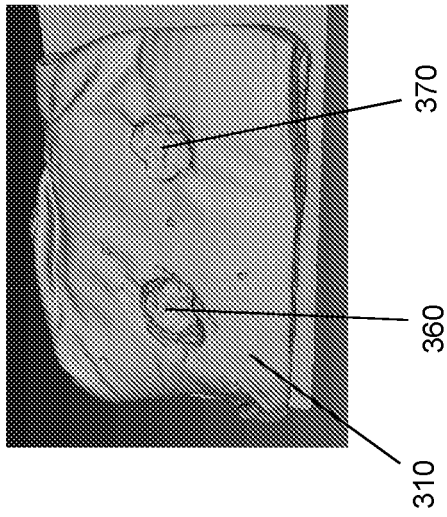
Figure 38:
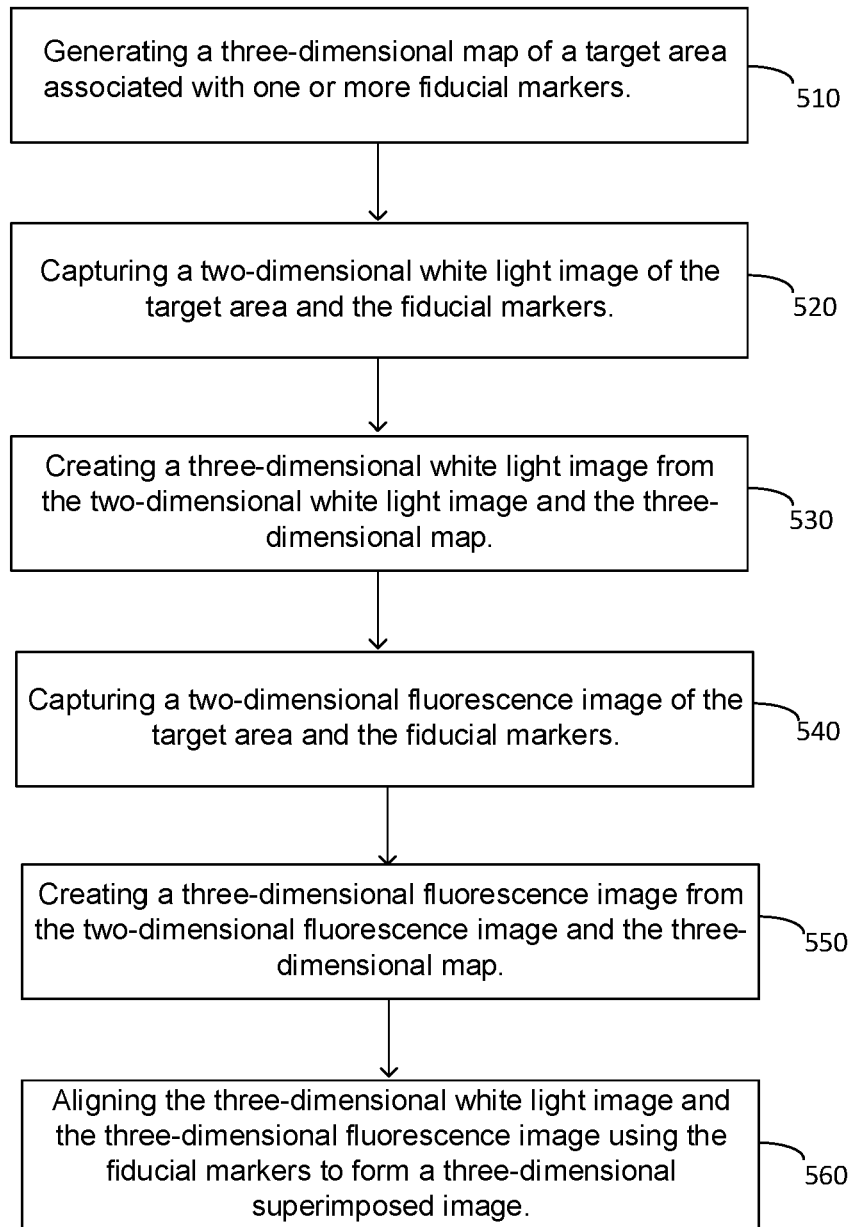
Figure 41:
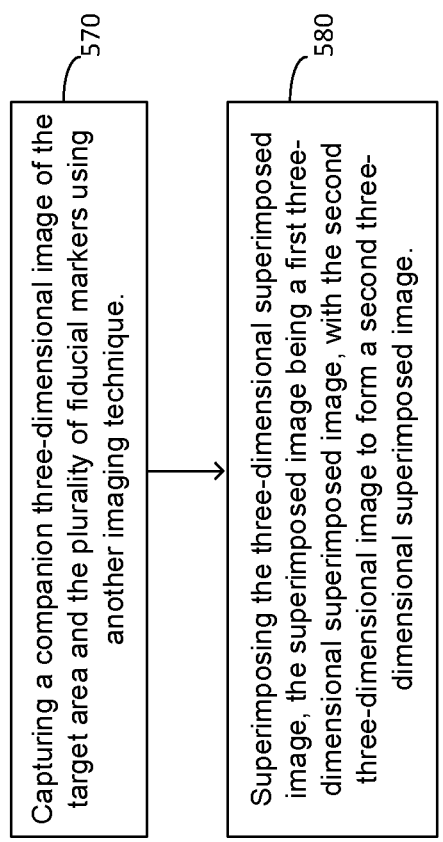

FIG. 12 is a perspective view of an embodiment of an imaging device of the present disclosure in a closed configuration corresponding, for example, to any one of first imaging device 210, second imaging device 410, and third imaging device 510. Door 214 is shown in a closed configuration flush with housing front surface 218. A handle 614 is mounted on a door front surface 616. Any style or number of handles can be employed. Pulling on handle 614 alone or in combination with pressing door release 350, for example, can permit a user to open door 214. An optional window 618 is shown set in door 214. Window 618 can be located elsewhere on housing 212 or omitted altogether. The number of components and their placement can be varied. The number and arrangement shown in FIG. 12 is an example.

The present disclosure includes the following aspects/embodiments/features in any order and/or in any combination:

A method of generating a three-dimensional image of a target using two-dimensional images obtained within an enclosed environment, comprising: while a target is positioned within the enclosed environment: generating a three-dimensional map of a target area associated with one or more fiducial markers; capturing a two-dimensional white light image of the target area and the fiducial markers; and capturing a two-dimensional fluorescence image of the target area and the one or more fiducial markers.

1. A method of generating a three-dimensional image of a target using two-dimensional images obtained within an enclosed environment, comprising:
   while a target is positioned within the enclosed environment:
   generating a three-dimensional map of a target area associated with one or more fiducial markers;
   capturing a two-dimensional white light image of the target area and the one or more fiducial markers; and
   capturing a two-dimensional fluorescence image of the target area and the one or more fiducial markers.
2. The method of any preceding or following embodiment/feature/aspect, wherein the capturing of the two-dimensional fluorescence image of the target area and the one or more fiducial markers comprises:
   illuminating the target area and the one or more fiducial markers with an excitation light, and
   receiving at least one fluorescence emission responsive to illumination of the target area with the excitation light.
3. The method of any preceding or following embodiment/feature/aspect, wherein the excitation light is between about 400 nm and about 450 nm.
4. The method of any preceding or following embodiment/feature/aspect, wherein the excitation light has a wavelength of about 405 nm.
5. The method of any preceding or following embodiment/feature/aspect, wherein the capturing of the two-dimensional fluorescence image of the target area and the one or more fiducial markers comprises capturing an emission of at least one fluorescent molecule.
6. The method of any preceding or following embodiment/feature/aspect, wherein the at least one fluorescent molecule comprises an endogenous molecule capable of fluorescing.
7. The method of any preceding or following embodiment/feature/aspect, wherein the at least one fluorescent molecule comprises an exogenous molecule capable of fluorescing or a molecule comprising an exogenously added moiety capable of fluorescing.
8. The method of any preceding or following embodiment/feature/aspect, wherein the at least one fluorescent molecule comprises aminolevulinic acid (ALA) induced porphyrins.
9. The method of any preceding or following embodiment/feature/aspect, wherein the three-dimensional map is generated using infrared light.
10. The method of any preceding or following embodiment/feature/aspect, wherein the three-dimensional map is generated using near infrared light.
11. The method of any preceding or following embodiment/feature/aspect, wherein generating the three-dimensional map comprises:
    projecting infrared radiation at the target area;
    receiving infrared radiation reflected by the target area; and
    measuring depth of the target area based on the reflected infrared radiation to generate the three-dimensional map.
12. The method of any preceding or following embodiment/feature/aspect, wherein the infrared radiation is projected as a beam split into a light pattern, the reflected infrared radiation comprises a distortion of the light pattern, and the depth is measured based on the distortion of the light pattern.
13. The method of any preceding or following embodiment/feature/aspect, wherein the light pattern is formed by a diffraction grating and the light pattern comprises a plurality of dots.
14. The method of any preceding or following embodiment/feature/aspect, wherein the depth is measured by time-of-flight based on a phase shift between the projected and the reflected infrared radiation.
15. The method of any preceding or following embodiment/feature/aspect, wherein the target comprises a tissue excised from a subject organism.
16. The method of any preceding or following embodiment/feature/aspect, wherein the tissue comprises a precancerous tissue, a cancerous tissue, or both.
17. The method of any preceding or following embodiment/feature/aspect, wherein the cancerous tissue comprises a tumor.
18. The method of any preceding or following embodiment/feature/aspect, wherein the tumor is a breast tumor and the excised tissue comprises a lumpectomy.
19. The method of any preceding or following embodiment/feature/aspect, wherein the excised tissue comprises a fluorescent molecule associated with a probe targeting a tumor receptor, an enzyme-activated fluorescent molecule, or a genetically modified oncolytic virus-induced fluorescence, or any combination thereof.
20. The method of any preceding or following embodiment/feature/aspect, wherein the tumor receptor comprises HER2, a folate receptor, CXCR4, a hormone receptor, an EGFR, or a VEGF, or a combination thereof; and the enzyme comprises a protease, a carbohydrase, a lipase, a transferase, an oxidoreductase, a matrix metalloprotease (MMP), a caspase, a cathepsin, a kallikrein, serine protease, isocitrate dehydrogenase, or an enzyme overexpressed by tumor cells, or a combination thereof.
21. The method of any preceding or following embodiment/feature/aspect, wherein the target comprises a tissue excised from a surgical bed.
22. The method of any preceding or following embodiment/feature/aspect, wherein the excised tissue, the surgical bed, or both comprises a cancerous tissue.
23. The method of any preceding or following embodiment/feature/aspect, further comprising: creating a three-dimensional white light image from the two-dimensional white light image and the three-dimensional map; creating a three-dimensional fluorescence image from the two-dimensional fluorescence image and the three-dimensional map; and aligning the three-dimensional white light image and the three-dimensional fluorescence image using the one or more fiducial markers to form a three-dimensional superimposed image.
24. The method of any preceding or following embodiment/feature/aspect, wherein the target is a first target comprising an excised tissue, and the method further comprises performing the method outside of the enclosed environment on a second target comprising a surgical bed from which the tissue is excised, the three-dimensional superimposed image of the first performance being a first three-dimensional superimposed image and the three-dimensional superimposed image of the second performance being a second three-dimensional superimposed image, the method further comprising comparing the first and second three-dimensional superimposed images to determine a fluorescent continuity between the excised tissue and the surgical bed based on an orientation of the excised tissue relative to the surgical bed.

25. The method of any preceding or following embodiment/feature/aspect, wherein the fluorescent continuity comprises one or more of a bacterially infected tissue, a virally infected tissue, a burn, a precancerous tissue, a cancerous tissue, a connective tissue, a muscle tissue, a blood vesicle, and a skin feature.

26. The method of any preceding or following embodiment/feature/aspect, wherein the fluorescent continuity corresponds to a compromised tissue and the method further comprises excising at least a portion of the compromised tissue from the surgical bed.

27. The method of any preceding or following embodiment/feature/aspect, further comprising:
capturing a companion three-dimensional image of the target area and the one or more fiducial markers using an imaging technique comprising one or more of computerized tomography (CT), magnetic resonance imaging (MRI), photoacoustic imaging, ultrasound, and optical coherence tomography; and
superimposing the three-dimensional superimposed image, the superimposed image being a first three-dimensional superimposed image, with the companion three-dimensional image to form a second three-dimensional superimposed image.

28. The method of any preceding or following embodiment/feature/aspect, wherein the one or more fiducial markers comprise a first set of fiducial markers and a second set of fiducial markers.

29. The method of any preceding or following embodiment/feature/aspect, wherein the companion three-dimensional image is captured using computerized tomography and the one or more fiducial markers comprise at least one fluorescent molecule and at least one CT contrast agent.

30. The method of any preceding or following embodiment/feature/aspect, wherein the companion three-dimensional image is captured using photoacoustic imaging, and the target area comprises a breast tumor and an anti-HER2 dual fluorescence-photoacoustic probe.

31. The method of any preceding or following embodiment/feature/aspect, wherein the method is performed in real time.

32. An imaging device comprising: a chamber comprising a door comprising an interior door wall, the chamber comprising a sidewall, a floor, and a ceiling, a sample platform configured to support a sample during imaging; an imaging system comprising: a fluorescence imaging subsystem, a visible light imaging subsystem, an infrared measuring subsystem, and at least one image sensor configured to detect radiation, and a data output system configured to receive the detected radiation and to output data associated with the detected radiation, wherein the sample platform and the imaging system are configured to move relative to one another to image the sample.

33. The imaging device of any preceding or following embodiment/feature/aspect, wherein the sample platform rotates about a central axis.

34. The imaging device of any preceding or following embodiment/feature/aspect, wherein the imaging system rotates about a central axis.

35. The imaging device of any preceding or following embodiment/feature/aspect, wherein the chamber in a closed position provides a substantially opaque barrier to visible light exterior to the chamber.

36. The imaging device of any preceding or following embodiment/feature/aspect, wherein the imaging system is associated with the chamber surface.

37. The imaging device of any preceding or following embodiment/feature/aspect, wherein the sample platform is optically transparent.

38. The imaging device of any preceding or following embodiment/feature/aspect, wherein the imaging system is a first imaging system and the imaging device further comprises a second imaging system, the first imaging system positioned to image the sample from above the sample platform and the second imaging system configured to image the sample from below the sample platform.

39. The imaging device of any preceding or following embodiment/feature/aspect, wherein the first imaging system is associated with a first rotatable frame positioned above the sample platform and the second imaging system is associated with a second rotatable frame located below the sample platform.

40. The imaging device of any preceding or following embodiment/feature/aspect, wherein the first rotatable frame comprises an arm to which the fluorescence subsystem, the visible light subsystem, and the infrared subsystem of the first imaging system are attached.

41. The imaging device of any preceding or following embodiment/feature/aspect, wherein the second rotatable frame comprises a disc to which the fluorescence subsystem, the visible light subsystem, and the infrared subsystem of the second imaging system are attached.

42. The imaging device of any preceding or following embodiment/feature/aspect, wherein the fluorescence subsystem, the visible light subsystem, and the infrared subsystem are separately controllable.

43. The imaging device of any preceding or following embodiment/feature/aspect, wherein the fluorescence subsystem, the visible light subsystem, and the infrared subsystem are configured to be activated in a predetermined sequence.

44. The imaging device of any preceding or following embodiment/feature/aspect, wherein the visible light subsystem is configured to deactivate during activation of the fluorescence subsystem, the infrared subsystem, or both.

45. The imaging device of any preceding or following embodiment/feature/aspect, wherein the sample platform comprises an orientation marker for placement of the sample on the sample platform with respect to a coordinate system.

46. The imaging device of any preceding or following embodiment/feature/aspect, wherein the sample platform comprises a fiducial marker.

47. The imaging device of any preceding or following embodiment/feature/aspect, wherein the sample platform comprises a plurality of fiducial markers.

48. The imaging device of any preceding or following embodiment/feature/aspect, further comprising a completion indicator configured to indicate that imaging of a sample is complete.

49. The imaging device of any preceding or following embodiment/feature/aspect, wherein the completion indicator comprises an audible signal, a visible signal, or both.

50. The imaging device of any preceding or following embodiment/feature/aspect further comprising a door lock, wherein the door lock is configured to engage during sample imaging and disengage upon completion of sample imaging.

51. The imaging device of any preceding or following embodiment/feature/aspect, wherein a transparency of the door is controllable.

52. The imaging device of any preceding or following embodiment/feature/aspect, wherein the transparency is adjustable to be substantially opaque during sample imaging.

53. The imaging device of any preceding or following embodiment/feature/aspect, wherein the door comprises a window and the window is controllable to be substantially opaque during sample imaging.

54. The imaging device of any preceding or following embodiment/feature/aspect further comprising a user interface or is operatively associated with the user interface, wherein the user interface permits a user to control a function of the imaging device.

55. The imaging device of any preceding or following embodiment/feature/aspect, wherein the function comprises selection of an imaging program, programming of an imaging cycle, imaging timer, door unlock, door lock, door transparency, data selection, data output, data display, data processing, temperature, sample identification, fluorophore identification, power control, password entry, or rotation speed, or any combination thereof.

56. The imaging device of any preceding or following embodiment/feature/aspect, wherein the fluorescence subsystem comprises: an excitation light source configured to emit a first radiation capable of exciting a fluorophore; a filter configured to prevent passage of reflected excitation light and permit passage of fluorescence emitted by the fluorophore; and an imaging lens.

57. The imaging device of any preceding or following embodiment/feature/aspect, wherein the visible light subsystem comprises a visible light source configured to emit a second radiation.

58. The imaging device of any preceding or following embodiment/feature/aspect, wherein the second radiation comprises white light.

59. The imaging device of any preceding or following embodiment/feature/aspect, wherein the second radiation comprises monochromatic visible light.

60. The imaging device of any preceding or following embodiment/feature/aspect, wherein the infrared subsystem comprises an infrared light source configured to emit a third radiation.

61. The imaging device of any preceding or following embodiment/feature/aspect, wherein the third radiation comprises infrared radiation.

62. The imaging device of any preceding or following embodiment/feature/aspect, wherein the infrared radiation comprises near infrared radiation.

63. The imaging device of any preceding or following embodiment/feature/aspect, wherein the at least one image sensor is configured to detect radiation comprising the fluorescence, reflected visible light, and reflected infrared light.

64. The imaging device of any preceding or following embodiment/feature/aspect, wherein the at least one sensor comprises at least two sensors.

65. The imaging device of any preceding or following embodiment/feature/aspect, wherein the at least two sensors comprise a first sensor configured to detect fluorescence and a second detector configured to detect reflected visible light.

66. The imaging device of any preceding or following embodiment/feature/aspect, wherein the at least one sensor comprises at least three sensors comprising a first sensor configured to detect fluorescence, a second detector configured to detect the reflected visible light, and a third sensor configured to detect reflected infrared light.

67. The imaging device of any preceding or following embodiment/feature/aspect, further comprising a common radiation source configured to operate with one or more of the light sources.

68. The imaging device of any preceding or following embodiment/feature/aspect, wherein the one or more light sources comprise a converter to convert source radiation emitted from the common radiation source to the first radiation, the second radiation, or the third radiation, or a combination thereof.

69. The imaging device of any preceding or following embodiment/feature/aspect, wherein the converter comprises a filter, a lens, a prism, a diffractor, or a quantum dot, or a combination thereof.

70. The imaging device of any preceding or following embodiment/feature/aspect, wherein the excitation light source comprises a first converter, the visible light source comprises a second converter, and the infrared light source comprises a third converter.

71. The imaging device of any preceding or following embodiment/feature/aspect, further comprising a display unit.

72. The imaging device of any preceding or following embodiment/feature/aspect, wherein the display unit is configured to display the data output by the data output system.

73. The imaging device of any preceding or following embodiment/feature/aspect, wherein the data comprises a three-dimensional image.

74. The imaging device of any preceding or following embodiment/feature/aspect, wherein the display unit comprises a touchscreen.

75. The imaging device of any preceding or following embodiment/feature/aspect, wherein the detected radiation comprises one or more of fluorescence, reflected visible light, and reflected infrared light.

76. The imaging device of any preceding or following embodiment/feature/aspect, wherein the detected radiation comprises fluorescence, reflected visible light, and reflected infrared light.

77. The imaging device of any preceding or following embodiment/feature/aspect, wherein the imaging device is configured to visualize a target area of the sample.

78. The imaging device of any preceding or following embodiment/feature/aspect, further comprising a processor, wherein the processor is configured to generate a three-dimensional map of the sample or a target area thereof.

79. The imaging device of any preceding or following embodiment/feature/aspect, wherein the three-dimensional map is generated from infrared light reflected from the target area.

80. The imaging device of any preceding or following embodiment/feature/aspect, wherein the processor is further configured to capture a two-dimensional visible light image of the target area based on the detected radiation.

81. The imaging device of any preceding or following embodiment/feature/aspect, wherein the processor is further configured to create a three-dimensional visible light image of the target area based on the three-dimensional map and the two-dimensional visible light image.

82. The imaging device of any preceding or following embodiment/feature/aspect, wherein the processor is further configured to capture a two-dimensional fluorescence image of the target area based on the detected radiation.

83. The imaging device of any preceding or following embodiment/feature/aspect, wherein the processor is further configured to create a three-dimensional fluorescence image of the target area based on the three-dimensional map and the two-dimensional fluorescence image.

84. The imaging device of any preceding or following embodiment/feature/aspect, wherein the processor is further configured to align a three-dimensional visible light image of the target area with a three-dimensional fluorescence image of the target area to form a three-dimensional superimposed image of the target area.

85. The imaging device of any preceding or following embodiment/feature/aspect, wherein the alignment is performed based on co-registration of one or more fiducial markers associated with the target area.

86. The imaging device of any preceding or following embodiment/feature/aspect further comprising at least one power source, wherein the power source comprises an internal power source, an external power source input, or both.

87. The imaging device of any preceding or following embodiment/feature/aspect, wherein one or both of the imaging system and the sample platform is rotatable about a central axis.

88. The imaging device of any preceding or following embodiment/feature/aspect further comprising a motor configured to rotate one or both of the imaging system and the sample platform.

89. The imaging device of any preceding or following embodiment/feature/aspect, wherein the motor comprises a first motor configured to rotate the imaging system and a second motor configured to rotate the sample platform.

90. The imaging device of any preceding or following embodiment/feature/aspect, wherein one or both of the imaging system and the sample platform is rotatable at a continuous speed, a variable speed, continuously, intermittently, or reversibly, or a combination thereof.

91. The imaging device of any preceding or following embodiment/feature/aspect, wherein one or both of the imaging system and the sample platform is rotatable at a speed from about 0.01 rpm to about 1,000 rpm.

92. The imaging device of any preceding or following embodiment/feature/aspect, wherein one or both of the imaging system and the sample platform is rotatable at a speed from about 1.0 rpm to about 100 rpm.

93. The imaging device of any preceding or following embodiment/feature/aspect, wherein the sample platform further comprises a sample restraint configured to maintain the sample in a fixed position relative to the sample platform during imaging.

94. The imaging device of any preceding or following embodiment/feature/aspect, wherein the sample platform, chamber surface, or both are coated with an antimicrobial agent.

95. The imaging device of any preceding or following embodiment/feature/aspect further comprising a sanitization system.

96. The imaging device of any preceding or following embodiment/feature/aspect, wherein the sanitization system comprises an autoclave function.

97. The imaging device of any preceding or following embodiment/feature/aspect, wherein the data output system further comprises a cable, cable port, or both configured to operably connect the imaging device to an external device, information network, or both.

98. The imaging device of any preceding or following embodiment/feature/aspect further comprising a data storage in communication with the data output system, the data storage configured to store data output by the data output system, wherein the data storage is integral or removable.

99. The imaging device of any preceding or following embodiment/feature/aspect, wherein the imaging device is configured to be placed on a benchtop.

100. The imaging device of any preceding or following embodiment/feature/aspect, wherein the imaging device is configured to perform the method of any preceding or following embodiment/feature/aspect.

Other embodiments will be apparent to those skilled in the art from consideration of the specification and practice of the present disclosure disclosed herein. It is intended that the specification and examples be considered as exemplary only. Various aspects of the disclosure are set forth in the following claims.

What is claimed is:

1. A method of generating a three-dimensional image of a target using two-dimensional images obtained within an enclosed environment, comprising:
    while a target is positioned within the enclosed environment:
        generating a three-dimensional map of a target area associated with one or more fiducial markers;
        capturing a two-dimensional white light image of the target area and the one or more fiducial markers;
        capturing a two-dimensional fluorescence image of the target area and the one or more fiducial markers;
        creating a three-dimensional white light image from the two-dimensional white light image and the three-dimensional map;
        creating a three-dimensional fluorescence image from the two-dimensional fluorescence image and the three-dimensional map; and
        aligning the three-dimensional white light image and the three-dimensional fluorescence image using the one or more fiducial markers to form a three-dimensional superimposed image.

2. The method of claim 1, wherein the capturing of the two-dimensional fluorescence image of the target area and the one or more fiducial markers comprises:
    illuminating the target area and the one or more fiducial markers with an excitation light, and
    receiving at least one fluorescence emission responsive to illumination of the target area with the excitation light.

3. The method of claim 2, wherein the excitation light is between about 400 nm and about 450 nm.

4. The method of claim 2, wherein the excitation light has a wavelength of about 405 nm.

5. The method of claim 1, wherein the capturing of the two-dimensional fluorescence image of the target area and the one or more fiducial markers comprises capturing an emission of at least one fluorescent molecule.

6. The method of claim 5, wherein the at least one fluorescent molecule comprises an endogenous molecule capable of fluorescing exogenous molecule capable of fluorescing, or a molecule comprising an exogenously added moiety capable of fluorescing.

7. The method of claim 5, wherein the at least one fluorescent molecule comprises aminolevulinic acid (ALA) induced porphyrins.

8. The method of claim 1, wherein generating the three-dimensional map comprises:
projecting infrared radiation at the target area;
receiving infrared radiation reflected by the target area; and
measuring depth of the target area based on the reflected infrared radiation to generate the three-dimensional map.

9. The method of claim 8, wherein the infrared radiation is projected as a beam split into a light pattern, the reflected infrared radiation comprises a distortion of the light pattern, and the depth is measured based on the distortion of the light pattern.

10. The method of claim 9, wherein the light pattern is formed by a diffraction grating and the light pattern comprises a plurality of dots.

11. The method of claim 8, wherein the depth is measured by time-of-flight based on a phase shift between the projected and the reflected infrared radiation.

12. The method of claim 1, wherein the target comprises a tissue excised from a subject organism.

13. The method of claim 12, wherein the tissue comprises a precancerous tissue, a cancerous tissue, or both.

14. The method of claim 13, wherein the cancerous tissue comprises a tumor.

15. The method of claim 14, wherein the tumor is a breast tumor and the excised tissue comprises a lumpectomy.

16. The method of claim 12, wherein the excised tissue comprises a fluorescent molecule associated with a probe targeting a tumor receptor, an enzyme-activated fluorescent molecule, or a genetically modified oncolytic virus-induced fluorescence, or any combination thereof.

17. The method of claim 16, wherein the tumor receptor comprises HER2, a folate receptor, CXCR4, a hormone receptor, an EGFR, or a VEGF, or a combination thereof; and the enzyme comprises a protease, a carbohydrase, a lipase, a transferase, an oxidoreductase, a matrix metalloprotease (MMP), a caspase, a cathepsin, a kallikrein, serine protease, isocitrate dehydrogenase, or an enzyme overexpressed by tumor cells, or a combination thereof.

18. The method of claim 1, wherein the target comprises a tissue excised from a surgical bed.

19. The method of claim 18, wherein the excised tissue, the surgical bed, or both comprises a cancerous tissue.

20. The method of claim 1, wherein the target is a first target comprising an excised tissue, and the method further comprises performing the method outside of the enclosed environment on a second target comprising a surgical bed from which the tissue is excised, the three-dimensional superimposed image of the first performance being a first three-dimensional superimposed image and the three-dimensional superimposed image of the second performance being a second three-dimensional superimposed image, the method further comprising comparing the first and second three-dimensional superimposed images to determine a fluorescent continuity between the excised tissue and the surgical bed based on an orientation of the excised tissue relative to the surgical bed.

21. The method of claim 20, wherein the fluorescent continuity comprises one or more of a bacterially infected tissue, a virally infected tissue, a burn, a precancerous tissue, a cancerous tissue, a connective tissue, a muscle tissue, a blood vesicle, and a skin feature.

22. The method of claim 20, wherein the fluorescent continuity corresponds to a compromised tissue and the method further comprises excising at least a portion of the compromised tissue from the surgical bed.

23. The method of claim 1, further comprising:
capturing a companion three-dimensional image of the target area and the one or more fiducial markers using an imaging technique comprising one or more of computerized tomography (CT), magnetic resonance imaging (MRI), photoacoustic imaging, ultrasound, and optical coherence tomography; and
superimposing the three-dimensional superimposed image, the superimposed image being a first three-dimensional superimposed image, with the companion three-dimensional image to form a second three-dimensional superimposed image.

24. The method of claim 23, wherein the companion three-dimensional image is captured using computerized tomography and the one or more fiducial markers comprise at least one fluorescent molecule and at least one CT contrast agent.

25. The method of claim 23, wherein the companion three-dimensional image is captured using photoacoustic imaging, and the target area comprises a breast tumor and an anti-HER2 dual fluorescence-photoacoustic probe.

26. The method of claim 1, wherein the method is performed in real time.

27. An imaging device comprising:
a chamber comprising a door comprising an interior door wall,
the chamber comprising a sidewall, a floor, and a ceiling,
a sample platform configured to support a sample during imaging;
an imaging system comprising:
a fluorescence imaging subsystem,
a visible light imaging subsystem,
an infrared measuring subsystem, and
at least one image sensor configured to detect radiation;
a processor, wherein the processor is configured to:
generate a three-dimensional map of a target area associated with one or more fiducial markers;
capture a two-dimensional white light image of the target area and the one or more fiducial markers;
capture a two-dimensional fluorescence image of the target area and the one or more fiducial markers;
create a three-dimensional white light image from the two-dimensional white light image and the three-dimensional map;
create a three-dimensional fluorescence image from the two-dimensional fluorescence image and the three-dimensional map; and
align a three-dimensional white light image and the three-dimensional fluorescence image using the one or more fiducial markers to form a three-dimensional superimposed image;

a data output system configured to receive the detected radiation and to output data associated with the detected radiation, and to display the three-dimensional superimposed image;

wherein the sample platform and the imaging system are configured to move relative to one another to image the sample, and wherein the sample platform and the imaging system are further configured to rotate about separate axes.

28. The imaging device of claim 27, wherein the chamber in a closed position provides a substantially opaque barrier to visible light exterior to the chamber.

29. The imaging device of claim 27, wherein the imaging system is associated with the chamber surface.

30. The imaging device of claim 27, wherein the sample platform is optically transparent.

31. The imaging device of claim 30, wherein the imaging system is a first imaging system and the imaging device further comprises a second imaging system, the first imaging system positioned to image the sample from above the sample platform and the second imaging system configured to image the sample from below the sample platform.

32. The imaging device of claim 31, wherein the first imaging system is associated with a first rotatable frame positioned above the sample platform and the second imaging system is associated with a second rotatable frame located below the sample platform.

33. The imaging device of claim 27, wherein the fluorescence imaging subsystem, the visible light imaging subsystem, and the infrared measuring subsystem are separately controllable.

34. The imaging device of claim 27, wherein the fluorescence imaging subsystem, the visible light imaging subsystem, and the infrared measuring subsystem are configured to be activated in a predetermined sequence.

35. The imaging device of claim 27, wherein the visible light imaging subsystem is configured to deactivate during activation of the fluorescence imaging subsystem, the infrared measuring subsystem, or both.

36. The imaging device of claim 27, wherein the sample platform comprises an orientation marker for placement of the sample on the sample platform with respect to a coordinate system.

37. The imaging device of claim 27, wherein the sample platform comprises at least one fiducial marker.

38. The imaging device of claim 27, further comprising a completion indicator configured to indicate that imaging of a sample is complete.

39. The imaging device of claim 38 further comprising a door lock, wherein the door lock is configured to engage during sample imaging and disengage upon completion of sample imaging.

40. The imaging device of claim 27, wherein a transparency of the door is controllable.

41. The imaging device of claim 40, wherein the transparency is adjustable to be substantially opaque during sample imaging.

42. The imaging device of claim 40, wherein the door comprises a window and the window is controllable to be substantially opaque during sample imaging.

43. The imaging device of claim 27, wherein the imaging system further comprises a user interface or is operatively associated with the user interface, wherein the user interface permits a user to control a function of the imaging device.

44. The imaging device of claim 43, wherein the function comprises selection of an imaging program, programing of an imaging cycle, imaging timer, door unlock, door lock, door transparency, data selection, data output, data display, data processing, temperature, sample identification, fluorophore identification, power control, password entry, or rotation speed, or any combination thereof.

45. The imaging device of claim 27, wherein the fluorescence imaging subsystem comprises:

an excitation light source configured to emit a first radiation capable of exciting a fluorophore;

a filter configured to prevent passage of reflected excitation light and permit passage of fluorescence emitted by the fluorophore; and an imaging lens.

46. The imaging device of claim 45, wherein the visible light imaging subsystem comprises a visible light source configured to emit a second radiation.

47. The imaging device of claim 46, wherein the second radiation comprises white light or monochromatic visible light.

48. The imaging device of claim 46, wherein the infrared measuring subsystem comprises an infrared light source configured to emit a third radiation.

49. The imaging device of claim 48, wherein the third radiation comprises infrared or near infrared radiation.

50. The imaging device of claim 27, wherein the at least one sensor comprises a first sensor configured to detect fluorescence and a second detector configured to detect reflected visible light.

51. The imaging device of claim 27, wherein the at least one sensor comprises at least three sensors comprising a first sensor configured to detect fluorescence, a second detector configured to detect the reflected visible light, and a third sensor configured to detect reflected infrared light.

52. The imaging device of claim 48, further comprising a common radiation source configured to operate with one or more of the light sources.

53. The imaging device of claim 52, wherein the one or more light sources comprise a converter to convert source radiation emitted from the common radiation source to the first radiation, the second radiation, or the third radiation, or a combination thereof.

54. The imaging device of claim 53, wherein the converter comprises a filter, a lens, a prism, a diffractor, or a quantum dot, or a combination thereof.

55. The imaging device of claim 53, wherein the excitation light source comprises a first converter, the visible light source comprises a second converter, and the infrared light source comprises a third converter.

56. The imaging device of claim 27, further comprising a display unit.

57. The imaging device of claim 56, wherein the display unit is configured to display the data output by the data output system.

58. The imaging device of claim 57, wherein the data comprises a three-dimensional image.

59. The imaging device of claim 56, wherein the display unit comprises a touchscreen.

60. The imaging device of claim 27, wherein the processor is further configured to capture a two-dimensional visible light image of the target area based on the detected radiation.

61. The imaging device of claim 60, wherein the processor is further configured to create a three-dimensional visible light image of the target area based on the three-dimensional map and the two-dimensional visible light image.

62. The imaging device of claim 27, wherein the processor is further configured to capture a two-dimensional fluorescence image of the target area based on the detected radiation.

63. The imaging device of claim 62, wherein the processor is further configured to create a three-dimensional fluorescence image of the target area based on the three-dimensional map and the two-dimensional fluorescence image.

64. The imaging device of claim 27, wherein the processor is further configured to align a three-dimensional visible light image of the target area with a three-dimensional fluorescence image of the target area to form a three-dimensional superimposed image of the target area.

65. The imaging device of claim 64, wherein the alignment is performed based on co-registration of one or more fiducial markers associated with the target area.

66. The imaging device of claim 27 further comprising at least one power source, wherein the power source comprises an internal power source, an external power source input, or both.

67. The imaging device of claim 27, wherein one or both of the imaging system and the sample platform is rotatable about a central axis.

68. The imaging device of claim 67 further comprising a motor configured to rotate one or both of the imaging system and the sample platform.

69. The imaging device of claim 68, wherein the motor comprises a first motor configured to rotate the imaging system and a second motor configured to rotate the sample platform.

70. The imaging device of claim 67, wherein one or both of the imaging system and the sample platform is rotatable at a speed from about 0.01 rpm to about 1,000 rpm.

71. The imaging device of claim 67, wherein one or both of the imaging system and the sample platform is rotatable at a speed from about 1.0 rpm to about 100 rpm.

72. The imaging device of claim 27, wherein the sample platform further comprises a sample restraint configured to maintain the sample in a fixed position relative to the sample platform during imaging.

73. The imaging device of claim 27, wherein the sample platform, chamber surface, or both are coated with an antimicrobial agent.

74. The imaging device of claim 27 further comprising a sanitization system.

75. The imaging device of claim 74, wherein the sanitization system comprises an autoclave function.

76. The imaging device of claim 27, wherein the data output system further comprises a cable, cable port, or both configured to operably connect the imaging device to an external device, information network, or both.

77. The imaging device of claim 27 further comprising a data storage in communication with the data output system, the data storage configured to store data output by the data output system, wherein the data storage is integral or removable.

78. The method of claim 1, wherein the three-dimensional map is generated using infrared light.

79. The imaging device of claim 27, further comprising a processor, wherein the processor is configured to generate a three-dimensional map of the sample or a target area thereof, wherein the three-dimensional map is generated from infrared light reflected from the target area.

80. A computing system for generating a three-dimensional image of a target using two-dimensional images obtained within an enclosed environment, comprising:

at least one sensor configured to:
  capture a two-dimensional white light image of the target area and the one or more fiducial markers; and
  capture a two-dimensional fluorescence image of the target area and the one or more fiducial markers; and
at least one processor connected to the at least one sensor, wherein the at least one processor is configured to:
  generate a three-dimensional map of a target area associated with one or more fiducial markers;
  receive the two-dimensional white light image and the two-dimensional fluorescence image from the at least one sensor;
  create a three-dimensional white light image from the two-dimensional white light image and the three-dimensional map;
  create a three-dimensional fluorescence image from the two-dimensional fluorescence image and the three-dimensional map; and
  align the three-dimensional white light image and the three-dimensional fluorescence image using the one or more fiducial markers to form a three-dimensional superimposed image.

81. An imaging device comprising:
a chamber comprising a sidewall, a floor, a ceiling, a door, and a sample platform positioned inside the chamber and configured to support a sample during imaging;
a first imaging system and a second imaging system, each of the first and second imaging systems comprising:
  a fluorescence imaging subsystem,
  a visible light imaging subsystem,
  an infrared measuring subsystem, and
  at least one image sensor configured to detect radiation;
a processor, wherein the processor is configured to:
  generate a three-dimensional map of a target area associated with one or more fiducial markers;
  capture a two-dimensional white light image of the target area and the one or more fiducial markers;
  capture a two-dimensional fluorescence image of the target area and the one or more fiducial markers;
  create a three-dimensional white light image from the two-dimensional white light image and the three-dimensional map;
  create a three-dimensional fluorescence image from the two-dimensional fluorescence image and the three-dimensional map; and
  align a three-dimensional white light image and the three-dimensional fluorescence image using the one or more fiducial markers to form a three-dimensional superimposed image; and
a data output system configured to receive the detected radiation and to output data associated with the detected radiation, and to display the three-dimensional superimposed image;
wherein the first imaging system is configured to image the sample from a first direction and the second imaging system is configured to image the sample from a second direction different from the first direction.

82. The imaging device of claim 81, wherein the device is configured to provide relative motion between the sample platform and the first and second imaging systems during imaging of a sample.

83. The imaging device of claim 81, wherein first direction is opposite to the second direction.

84. The imaging device of claim 83, wherein the sample platform is transparent.

85. The imaging device of claim 84, wherein the first imaging system is positioned to image the sample from above the sample platform and the second imaging system is positioned to image the sample from below the sample platform.

\* \* \* \* \*